United States Patent
Barnes et al.

(10) Patent No.: US 8,052,606 B2
(45) Date of Patent: *Nov. 8, 2011

(54) BALANCE BODY ULTRASOUND SYSTEM

(75) Inventors: Stephanie A. Barnes, Bothell, WA (US);
Steven M. Bunce, Sedro Woolley, WA (US);
Bryan S. Cabatic, Seattle, WA (US);
Blake W. Little, Bothell, WA (US);
Bill Purdue, Mill Creek, WA (US);
John D. Schultz, Bothell, WA (US);
Kari L. Rice, Bothell, WA (US)

(73) Assignee: SonoSite, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/771,982

(22) Filed: Apr. 30, 2010

(65) Prior Publication Data

US 2010/0274131 A1    Oct. 28, 2010

Related U.S. Application Data

(63) Continuation of application No. 10/099,474, filed on Mar. 15, 2002, now Pat. No. 7,819,807, which is a continuation-in-part of application No. 10/062,179, filed on Feb. 1, 2002, now Pat. No. 6,962,566, which is a continuation of application No. 09/840,002, filed on Apr. 19, 2001, now Pat. No. 6,569,101, and a continuation-in-part of application No. 09/630,165, filed on Aug. 1, 2000, now Pat. No. 6,416,475, which is a continuation-in-part of application No. 09/167,964, filed on Oct. 6, 1998, now Pat. No. 6,135,961, which is a continuation-in-part of application No. 08/863,937, filed on May 27, 1997, now Pat. No. 5,817,024, and a continuation-in-part of application No. 08/826,543, filed on Apr. 3, 1997, now Pat. No. 5,893,363, which is a continuation-in-part of application No. 08/672,782, filed on Jun. 28, 1996, now Pat. No. 5,722,412, application No. 08/863,937, which is a continuation-in-part of application No. 08/672,782.

(51) Int. Cl.
*A61B 8/00* (2006.01)
(52) U.S. Cl. ......... 600/443; 600/437; 600/459; 600/447
(58) Field of Classification Search ........... 600/437–463
See application file for complete search history.

(56) References Cited

U.S. PATENT DOCUMENTS 3,626,417 A    12/1971    Gilbert
(Continued)

FOREIGN PATENT DOCUMENTS

CN    1113009 A    12/1995
(Continued)

OTHER PUBLICATIONS

International Preliminary Examination Report, issued for PCT/US02/13386, dated Apr. 5, 2010, 7 pgs.

(Continued)

*Primary Examiner* — Sanjay Cattungal
(74) *Attorney, Agent, or Firm* — Perkins Coie LLP

(57) ABSTRACT

The present invention relates to a hand held ultrasound system having a balance body, a transducer assembly connected to said balance body via a communication means and a plurality of control elements arranged in an ergonomic fashion on said balance body, such that a user may hold said system and operate at least one of said control elements with the same hand. In particular a medical ultrasound system comprising a balance body incorporating system electronics, a power supply and a user interface wherein the user interface comprises a D-controller and a touch screen and a transducer assembly attached to the balanced body by a cable. The present invention relates to a hand held ultrasound system having a balance body, a transducer assembly connected to said balance body via a communication means and a plurality of control elements arranged in an ergonomic fashion on said balance body, such that a user may hold said system and operate at least one of said control elements with the same hand. In particular a medical ultrasound system comprising a balance body incorporating system electronics, a power supply and a user interface wherein the user interface comprises a D-controller and a touch screen and a transducer assembly attached to the balanced body by a cable.

25 Claims, 23 Drawing Sheets

U.S. PATENT DOCUMENTS

| | | |
|---|---|---|
| 3,964,296 A | 6/1976 | Matzuk |
| 3,965,296 A | 6/1976 | Miller |
| 4,154,113 A | 5/1979 | Engeler |
| 4,173,007 A | 10/1979 | McKeighen et al. |
| 4,413,629 A | 11/1983 | Durley, III |
| 4,561,019 A | 12/1985 | Lizzi et al. |
| 4,649,930 A | 3/1987 | Groch et al. |
| 5,123,415 A | 6/1992 | Daigle |
| 5,143,105 A | 9/1992 | Katayama |
| 5,154,113 A | 10/1992 | Marquez |
| 5,156,152 A | 10/1992 | Yamazaki et al. |
| 5,163,434 A | 11/1992 | Kumazawa |
| 5,197,477 A | 3/1993 | Peterson et al. |
| 5,293,351 A | 3/1994 | Noponen |
| 5,295,485 A | 3/1994 | Shinomura et al. |
| 5,345,426 A | 9/1994 | Lipschutz |
| 5,360,005 A | 11/1994 | Wilk |
| 5,369,624 A | 11/1994 | Fukukita et al. |
| 5,373,317 A | 12/1994 | Salvati et al. |
| 5,388,079 A | 2/1995 | Kim et al. |
| 5,394,875 A | 3/1995 | Lewis et al. |
| 5,413,105 A | 5/1995 | Forestieri |
| 5,414,803 A | 5/1995 | Malzbender |
| 5,419,330 A | 5/1995 | Nishigaki et al. |
| 5,427,111 A | 6/1995 | Traub et al. |
| 5,437,281 A | 8/1995 | Lin et al. |
| 5,460,180 A | 10/1995 | Klepper et al. |
| 5,465,011 A | 11/1995 | Miller et al. |
| 5,495,137 A | 2/1996 | Park et al. |
| 5,520,187 A | 5/1996 | Snyder |
| 5,546,807 A | 8/1996 | Oxaal et al. |
| 5,551,434 A | 9/1996 | Iinuma |
| 5,555,534 A | 9/1996 | Maslak et al. |
| 5,588,435 A | 12/1996 | Weng et al. |
| 5,590,658 A | 1/1997 | Chiang et al. |
| 5,594,807 A | 1/1997 | Liu |
| 5,617,864 A | 4/1997 | Stouffer et al. |
| 5,623,930 A | 4/1997 | Wright et al. |
| 5,628,321 A | 5/1997 | Scheib et al. |
| 5,634,465 A | 6/1997 | Schmiesing et al. |
| 5,640,960 A | 6/1997 | Jones et al. |
| 5,642,732 A | 7/1997 | Wang |
| 5,647,366 A | 7/1997 | Weng |
| 5,655,535 A | 8/1997 | Friemel et al. |
| 5,655,536 A | 8/1997 | Takamizawa |
| 5,690,114 A | 11/1997 | Chiang et al. |
| 5,697,372 A | 12/1997 | Hughes |
| 5,709,209 A | 1/1998 | Friemel et al. |
| 5,722,412 A | 3/1998 | Pflugrath et al. |
| 5,724,974 A | 3/1998 | Goodsell, Jr. et al. |
| 5,732,705 A | 3/1998 | Yokoyama et al. |
| 5,763,785 A | 6/1998 | Chiang |
| 5,769,079 A | 6/1998 | Hossack |
| 5,782,769 A | 7/1998 | Hwang et al. |
| 5,785,655 A | 7/1998 | Goodsell, Jr. et al. |
| 5,795,297 A | 8/1998 | Daigle |
| 5,797,847 A | 8/1998 | Miller et al. |
| 5,817,024 A | 10/1998 | Ogle et al. |
| 5,826,042 A | 10/1998 | Kirkendoll |
| 5,839,442 A | 11/1998 | Chiang et al. |
| 5,846,202 A | 12/1998 | Ramamurthy et al. |
| 5,860,924 A | 1/1999 | Quistgaard |
| 5,860,931 A | 1/1999 | Chandler |
| 5,891,037 A | 4/1999 | Hossack et al. |
| 5,893,363 A | 4/1999 | Little et al. |
| 5,935,074 A | 8/1999 | Mo et al. |
| 5,964,709 A | 10/1999 | Chiang et al. |
| 6,048,319 A | 4/2000 | Hudgins et al. |
| 6,050,942 A | 4/2000 | Rust et al. |
| 6,054,922 A | 4/2000 | Smith |
| 6,083,156 A | 7/2000 | Lisiecki |
| 6,095,980 A | 8/2000 | Burns et al. |
| 6,126,608 A | 10/2000 | Kemme et al. |
| 6,135,961 A | 10/2000 | Pflugrath et al. |
| 6,171,246 B1 | 1/2001 | Averkiou et al. |
| 6,203,498 B1 | 3/2001 | Bunce et al. |
| 6,248,073 B1 | 6/2001 | Gilbert et al. |
| 6,251,073 B1 | 6/2001 | Imran et al. |
| 6,383,139 B1 | 5/2002 | Hwang et al. |
| 6,416,475 B1 | 7/2002 | Hwang et al. |
| D462,446 S | 9/2002 | Felix et al. |
| 6,447,451 B1 | 9/2002 | Wing et al. |
| D467,002 S | 12/2002 | Felix et al. |
| 6,490,684 B1 | 12/2002 | Fenstemaker et al. |
| D469,539 S | 1/2003 | Felix et al. |
| D469,877 S | 2/2003 | Felix et al. |
| 6,530,887 B1 | 3/2003 | Gilbert et al. |
| 6,532,152 B1 | 3/2003 | White et al. |
| 6,561,979 B1 | 5/2003 | Wood et al. |
| 6,569,101 B2 | 5/2003 | Quistgaard et al. |
| 6,569,102 B2 | 5/2003 | Imran et al. |
| 6,575,908 B2 | 6/2003 | Barnes et al. |
| 6,618,206 B2 | 9/2003 | Tarakci et al. |
| 6,663,567 B2 | 12/2003 | Ji et al. |
| 6,685,645 B1 | 2/2004 | McLaughlin et al. |
| 6,733,455 B2 | 5/2004 | Mo et al. |
| 6,773,399 B2 | 8/2004 | Xi et al. |
| 6,866,631 B2 | 3/2005 | McLaughlin et al. |
| 6,866,632 B1 | 3/2005 | Chou et al. |
| 6,896,658 B2 | 5/2005 | Ji et al. |
| 6,936,008 B2 | 8/2005 | Tarakci et al. |
| 6,962,566 B2 | 11/2005 | Quistgaard et al. |
| 6,980,419 B2 | 12/2005 | Smith et al. |
| 7,022,075 B2 | 4/2006 | Grunwald et al. |
| 7,115,093 B2 | 10/2006 | Halmann et al. |
| 7,604,596 B2 | 10/2009 | Hwang et al. |
| 7,686,766 B2 | 3/2010 | Quistgaard et al. |
| 7,740,586 B2 | 6/2010 | Hwang et al. |
| 7,819,807 B2 | 10/2010 | Barnes et al. |
| 2002/0169378 A1 | 11/2002 | Mo et al. |
| 2002/0173344 A1 | 11/2002 | Cupps et al. |
| 2002/0173721 A1 | 11/2002 | Grunwald et al. |
| 2002/0177774 A1 | 11/2002 | Hwang et al. |
| 2003/0004414 A1 | 1/2003 | McLaughlin et al. |
| 2003/0009102 A1 | 1/2003 | Quistgaard et al. |
| 2003/0013959 A1 | 1/2003 | Grunwald et al. |
| 2003/0013965 A1 | 1/2003 | Quistgaard et al. |
| 2003/0195418 A1 | 10/2003 | Barnes et al. |
| 2004/0138569 A1 | 7/2004 | Grunwald et al. |
| 2005/0131294 A1 | 6/2005 | Ji et al. |
| 2006/0025684 A1 | 2/2006 | Quistgaard et al. |
| 2006/0116578 A1 | 6/2006 | Grunwald et al. |
| 2010/0121196 A1 | 5/2010 | Hwang et al. |

FOREIGN PATENT DOCUMENTS

| | | |
|---|---|---|
| CN | 1170560 A | 1/1998 |
| CN | 1189217 A | 7/1998 |
| EP | 0713102 A1 | 5/1996 |
| EP | 0763344 A2 | 3/1997 |
| EP | 0815793 A2 | 1/1998 |
| JP | 53059283 A | 5/1978 |
| JP | 55151952 A | 11/1980 |
| JP | 59500650 T | 4/1984 |
| JP | 62227326 A | 10/1987 |
| JP | 03234246 A | 10/1991 |
| JP | 07051270 A | 2/1995 |
| JP | 07067879 A | 3/1995 |
| JP | 07079981 A | 3/1995 |
| JP | 07124160 A | 5/1995 |
| JP | 07222744 A | 8/1995 |
| JP | 07325908 A | 12/1995 |
| JP | 08038473 A | 2/1996 |
| JP | 08112279 A | 5/1996 |
| JP | 08117227 A | 5/1996 |
| JP | 08505556 T | 6/1996 |
| JP | 08173431 A | 7/1996 |
| JP | 08224237 A | 9/1996 |
| JP | 09000526 A | 1/1997 |
| JP | 09039728 A | 2/1997 |
| JP | 10057375 A | 3/1998 |
| WO | 94/23421 A1 | 10/1994 |
| WO | 9603919 A1 | 2/1996 |
| WO | 9604588 A1 | 2/1996 |
| WO | 9624053 A1 | 8/1996 |
| WO | 97/01768 A2 | 1/1997 |
| WO | 01/13796 A1 | 3/2001 |
| WO | 2004/080364 A2 | 9/2004 |

OTHER PUBLICATIONS

Appeal Decision issued Dec. 4, 2006 in Japan Application No. 97-185976, 9 pages.
Armitage, A.D. et al., "An Integrated Array Transducer Receiver for Ultrasound Imaging," Sensors and Actuators A, vol. 47, No. 1-3, pp. 542-546, Mar. 4, 1995, ISSN: 0924-4247.
Decision of Rejection issued Feb. 10, 2004 in Japan Application No. 97-185976, 1 page.
Decision on Rejection issued Jun. 25, 2004 in China Application No. 8108973.9, 9 pages.
Decision on Rejection issued May 9, 2008 in China Application No. 97113678.5, 8 pages.
Examination Report issued Apr. 1, 2003 in European Application No. 97304656.8, 3 pages.
Examination Report issued Jun. 29, 2004 in European Application No. 99942250.4, 2 pages.
Examination Report issued May 7, 2002 in European Application No. 98304152.6, 6 pages.
Examination Report issued Sep. 12, 2002 in European Application No. 973044656.8, 4 pages.
Examination Report issued Sep. 4, 2003 in European Application No. 98302606.3, 4 pages.
Final Office Action issued Mar. 16, 2010 in Japan Application No. 10-107154, 6 pages.
Hatfield, J.V. et al., "High Frequency Ultrasonic Scanning System," 38th Midwest Symposium on Circuits and Systems: Proceedings, Rio de Janeiro, Aug. 13-16, 1995, vol. 2, No. Symp. 38, pp. 1175-1178.
Hwang, J.J. et al., "Portable Ultrasound Device for Battlefield Trauma," 1998 IEEE Ultrasonics Symposium Proceedings, vol. 2, pp. 1663-1667, Oct. 5, 1998, ISBN: 0-7803-4096-5.
International Preliminary Examination Report issued Mar. 19, 2010 in International Application No. PCT/US2002/013386, 4 pages.
International Preliminary Examination Report issued Nov. 7, 2000 in International Application No. PCT/US1999/018661, 5 pages.
International Search Report issued Nov. 18, 1999 in International Application No. PCT/US1999/018661, 3 pages.
International Search Report issued Nov. 3, 2003 in International Application No. PCT/US2002/013386, 3 pages.
Kim, J.H. et al., "Pipelined Sampled-Delay Focusing in Ultrasound Imaging Systems," Ultrasonic Imaging, vol. 9, No. 2, pp. 57-91, Apr. 1987, ISSN: 0161-7346.
Notice of Reasons for Rejection issued Jul. 8, 2003 in Japan Application No. 97-185976, 2 pages.
Notice of Reasons for Rejection issued Nov. 12, 2002 in Japan Application No. 97-185976, 4 pages.
Office Action issued Apr. 1, 2008 in U.S. Appl. No. 11/206,244, 8 pages.
Office Action issued Apr. 30, 2004 in Korea Application No. 1997-0028534, 4 pages.
Office Action issued Apr. 8, 2005 in China Application No. 98106133.8, 12 pages.
Office Action issued Apr. 8, 2008 in Japan Application No. 10-107154, 6 pages.
Office Action issued Aug. 18, 1997 in U.S. Appl. No. 08/672,782, 4 pages.
Office Action issued Aug. 19, 2004 in U.S. Appl. No. 10/062,179, 5 pages.
Office Action issued Aug. 27, 2008 in U.S. Appl. No. 10/404,220, 11 pages.
Office Action issued Aug. 29, 2006 in U.S. Appl. No. 10/099,474, 6 pages.
Office Action issued Aug. 30, 2000 in U.S. Appl. No. 09/306,372, 9 pages.
Office Action issued Aug. 5, 2005 in China Application No. 98108973.9, 7 pages.
Office Action issued Dec. 13, 2001 in U.S. Appl. No. 09/630,165, 3 pages.
Office Action issued Dec. 19, 1997 in U.S. Appl. No. 08/863,937, 7 pages.
Office Action issued Dec. 29, 2010 in U.S. Appl. No. 12/692,483, 7 pages.
Office Action issued Feb. 12, 2007 in U.S. Appl. No. 10/099,474, 7 pages.
Office Action issued Feb. 24, 1997 in U.S. Appl. No. 08/672,782, 6 pages.
Office Action issued Feb. 24, 2006 in U.S. Appl. No. 10/099,474, 6 pages.
Office Action issued Feb. 6, 2003 in U.S. Appl. No. 10/151,583, 6 pages.
Office Action issued Jan. 18, 2008 in China Application No. 97113678.5, 8 pages.
Office Action issued Jan. 19, 2005 in U.S. Appl. No. 10/062,179, 7 pages.
Office Action issued Jan. 20, 2005 in Korea Application No. 1997-0028534, 4 pages.
Office Action issued Jan. 27, 2009 in Japan Application No. 10-107154, 9 pages.
Office Action issued Jan. 7, 2009 in U.S. Appl. No. 11/206,244, 8 pages.
Office Action issued Jul. 10, 2009 in U.S. Appl. No. 10/099,474, 8 pages.
Office Action issued Jul. 25, 2003 in China Application No. 98108973.9, 10 pages.
Office Action issued Jul. 25, 2003 in U.S. Appl. No. 10/151,583, 8 pages.
Office Action issued Jul. 5, 2001 in U.S. Appl. No. 09/426,088, 7 pages.
Office Action issued Jun. 1, 2004 in U.S. Appl. No. 10/099,474, 9 pages.
Office Action issued Jun. 1, 2006 in U.S. Appl. No. 10/745,827, 5 pages.
Office Action issued Jun. 21, 2005 in Korea Application No. 1998-0019208, 6 pages.
Office Action issued Mar. 11, 2008 in U.S. Appl. No. 10/099,474, 6 pages.
Office Action issued Mar. 11, 2008 in U.S. Appl. No. 10/404,220, 10 pages.
Office Action issued Mar. 12, 2007 in Canada Application No. 2,341,099, 3 pages.
Office Action issued Mar. 15, 2002 in U.S. Appl. No. 09/840,002, 5 pages.
Office Action issued Mar. 23, 2005 in U.S. Appl. No. 10/099,474, 7 pages.
Office Action issued Mar. 31, 2006 in Norway Application No. 19981475, 3 pages.
Office Action issued Mar. 31, 2006 in Norway Application No. 19982389, 3 pages.
Office Action issued Mar. 5, 2004 in China Application No. 98108973.9, 10 pages.
Office Action issued May 16, 2005 in Korea Application No. 1998-0011808, 5 pages.
Office Action issued Nov. 16, 2006 in U.S. Appl. No. 10/745,827, 4 pages.
Office Action issued Nov. 18, 1997 in U.S. Appl. No. 08/826,543, 7 pages.
Office Action issued Oct. 1, 2008 in U.S. Appl. No. 10/099,474, 7 pages.
Office Action issued Oct. 17, 2005 in Korea Application No. 1998-0019208, 4 pages.
Office Action issued Oct. 18, 2007 in U.S. Appl. No. 10/404,220, 7 pages.
Office Action issued Oct. 31, 2006 in U.S. Appl. No. 10/404,220, 6 pages.
Office Action issued Sep. 22, 2005 in U.S. Appl. No. 10/099,474, 6 pages.
Office Action issued Sep. 5, 2003 in China Application No. 97113678.5, 8 pages.
Office Action issued Sep. 6, 2010 in China Application No. 200910004074.1, 15 pages.
Office Action issued Sep. 9, 2005 in China Application No. 98106133.8, 6 pages.
Reexamination Decision issued Jan. 19, 2005 in China Application No. 98108973.9, 2 pages.

Search Report issued Feb. 11, 2004 in European Application No. 99942250.4, 2 pages.
Search Report issued Nov. 5, 1999 in European Application No. 98302303.3, 4 pages.
Search Report issued Sep. 16, 1999 in European Application No. 98304152.6 4 pages.
Search Report issued Sep. 3, 1999 in European Application No. 97304656.8, 3 pages.
Volder, J.E., "The CORDIC Trigonometric Computing Technique", IRE Transactions on Electronic Computers, 1959, pp. 330-334.
Written Opinion issued Aug. 23, 2000 in International Application No. PCT/US1999/018661, 5 pages.

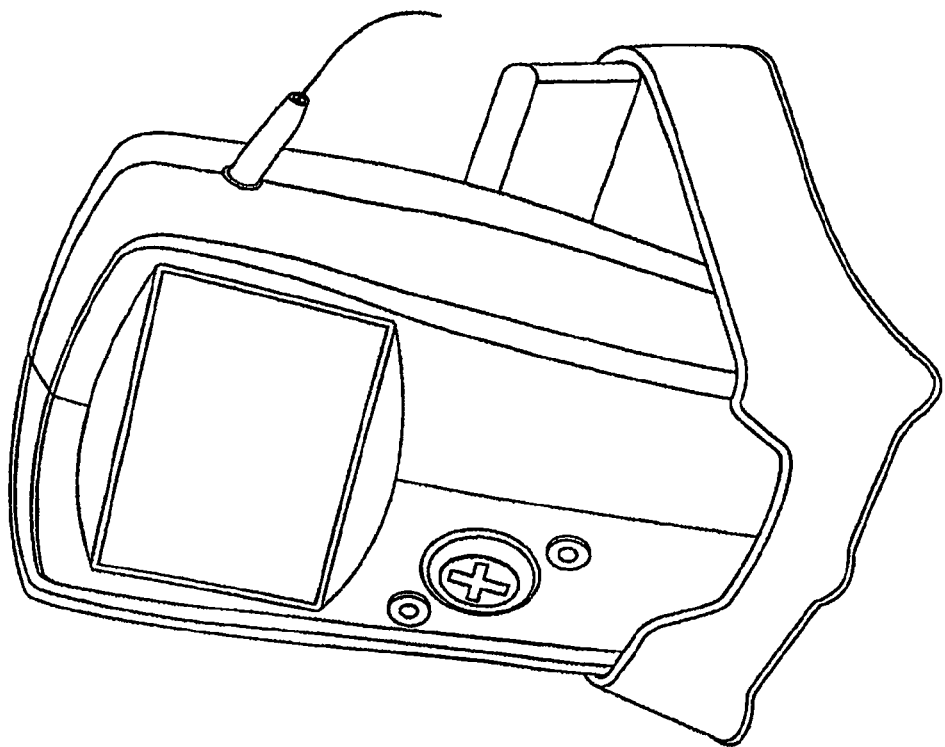
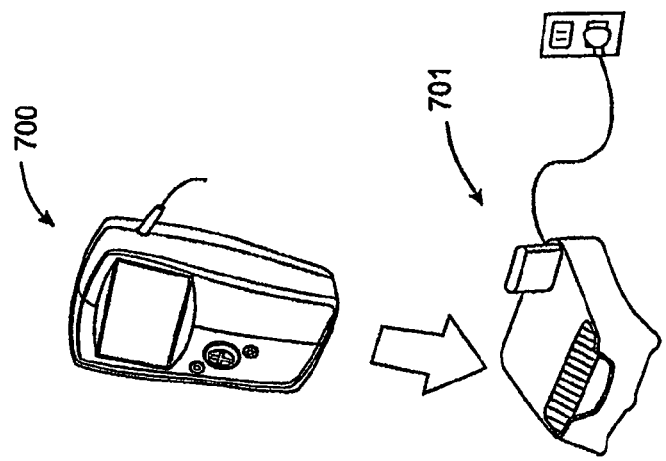
FIG. 7B
FIG. 7A

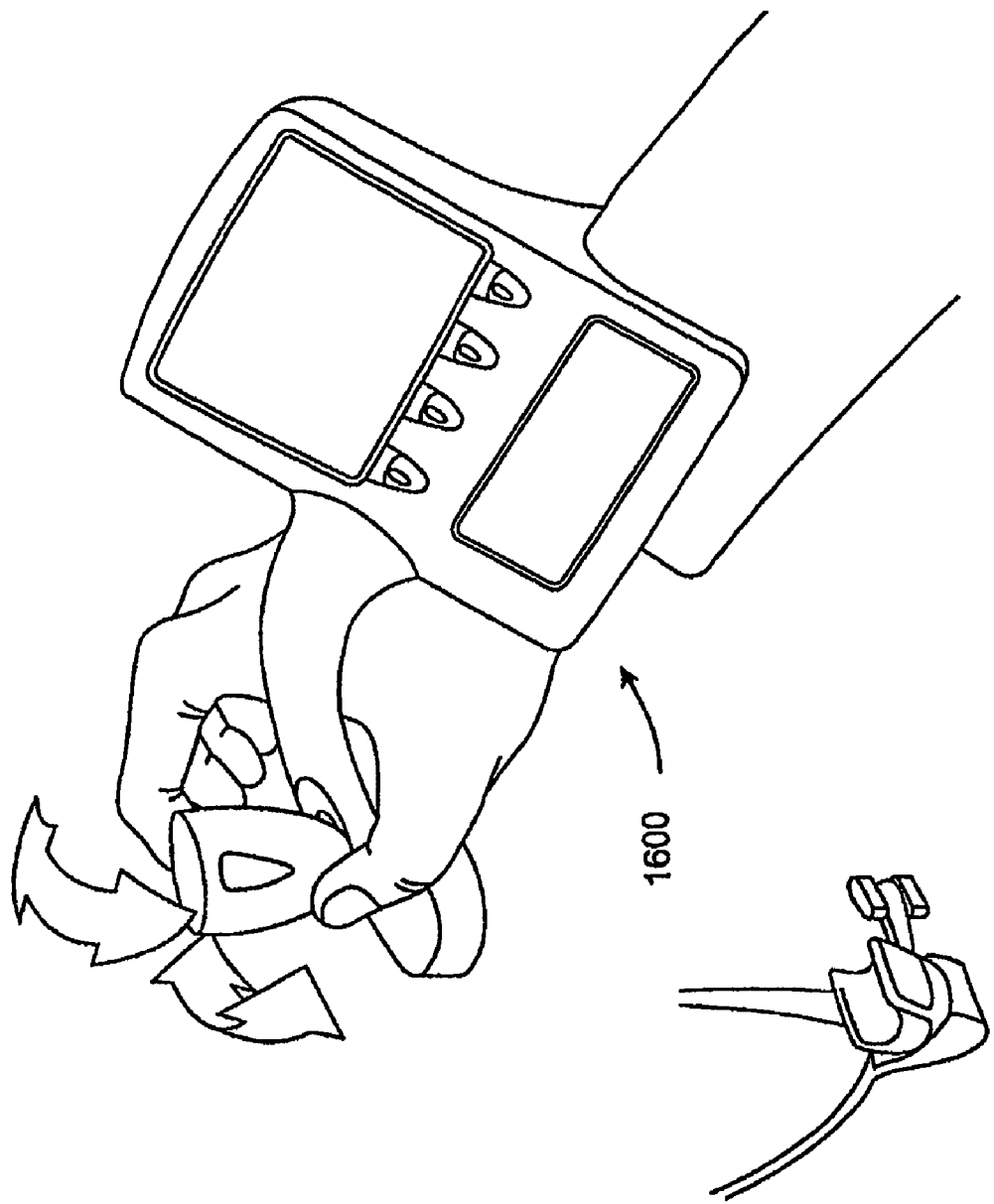

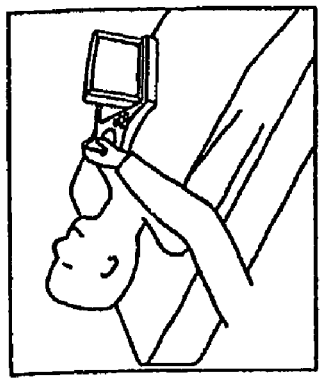
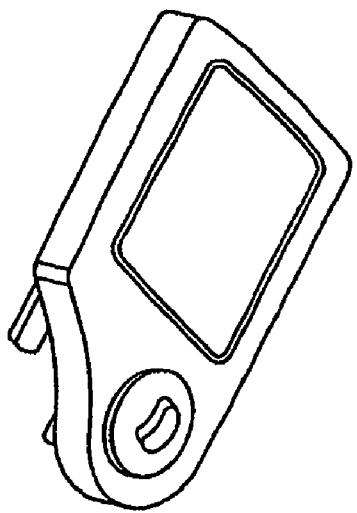
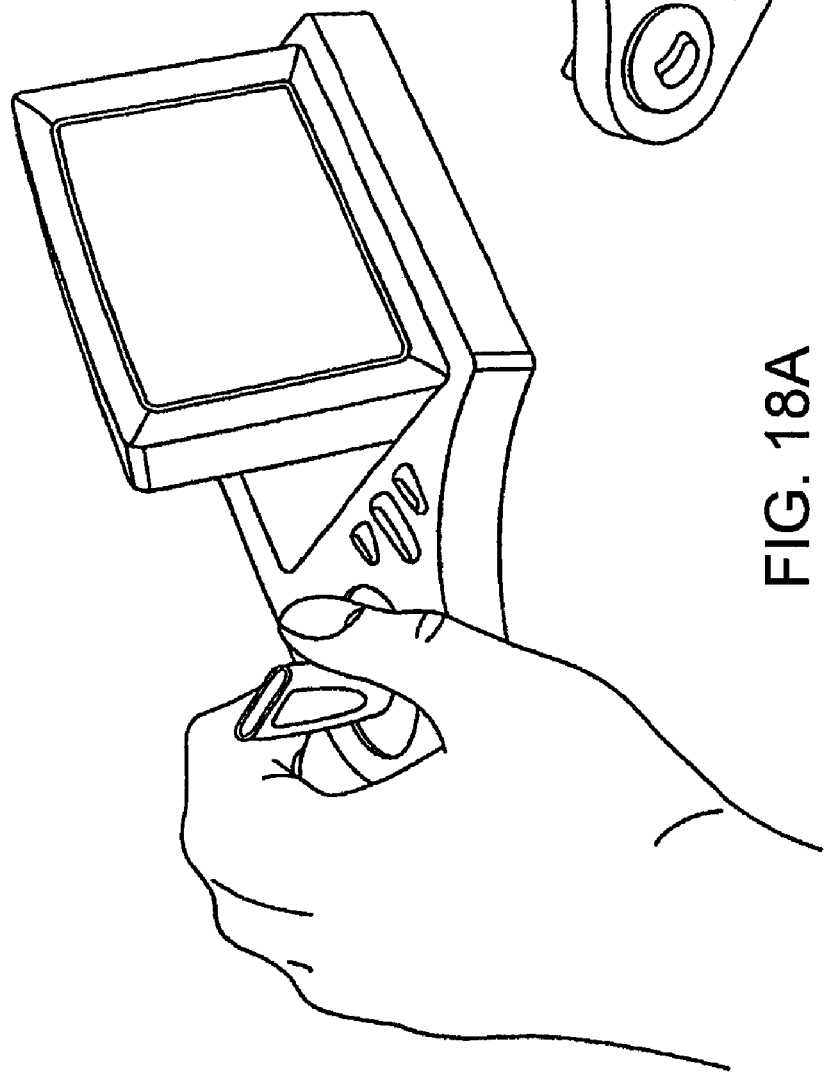
FIG. 18C
FIG. 18B
FIG. 18A
1800

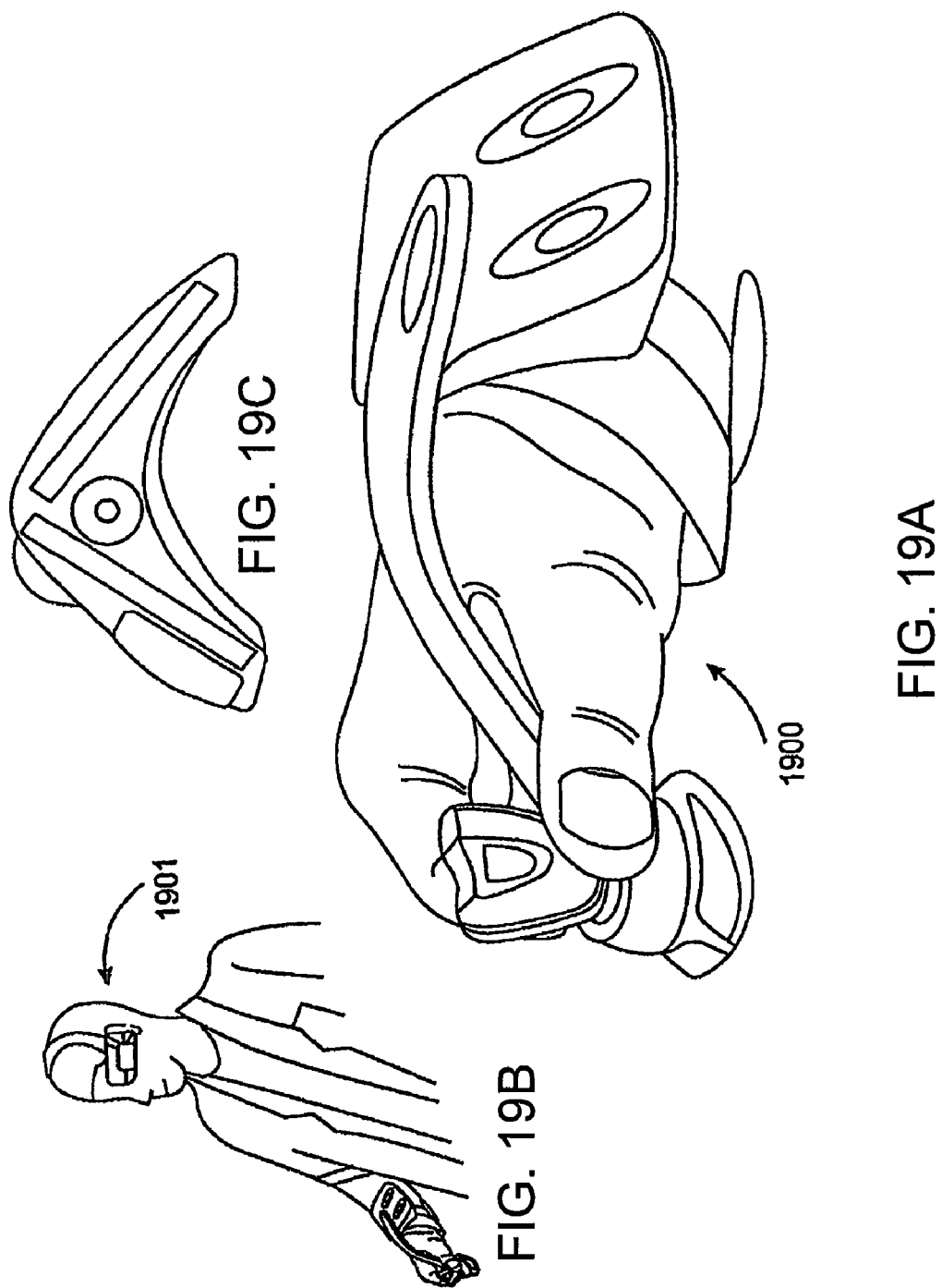

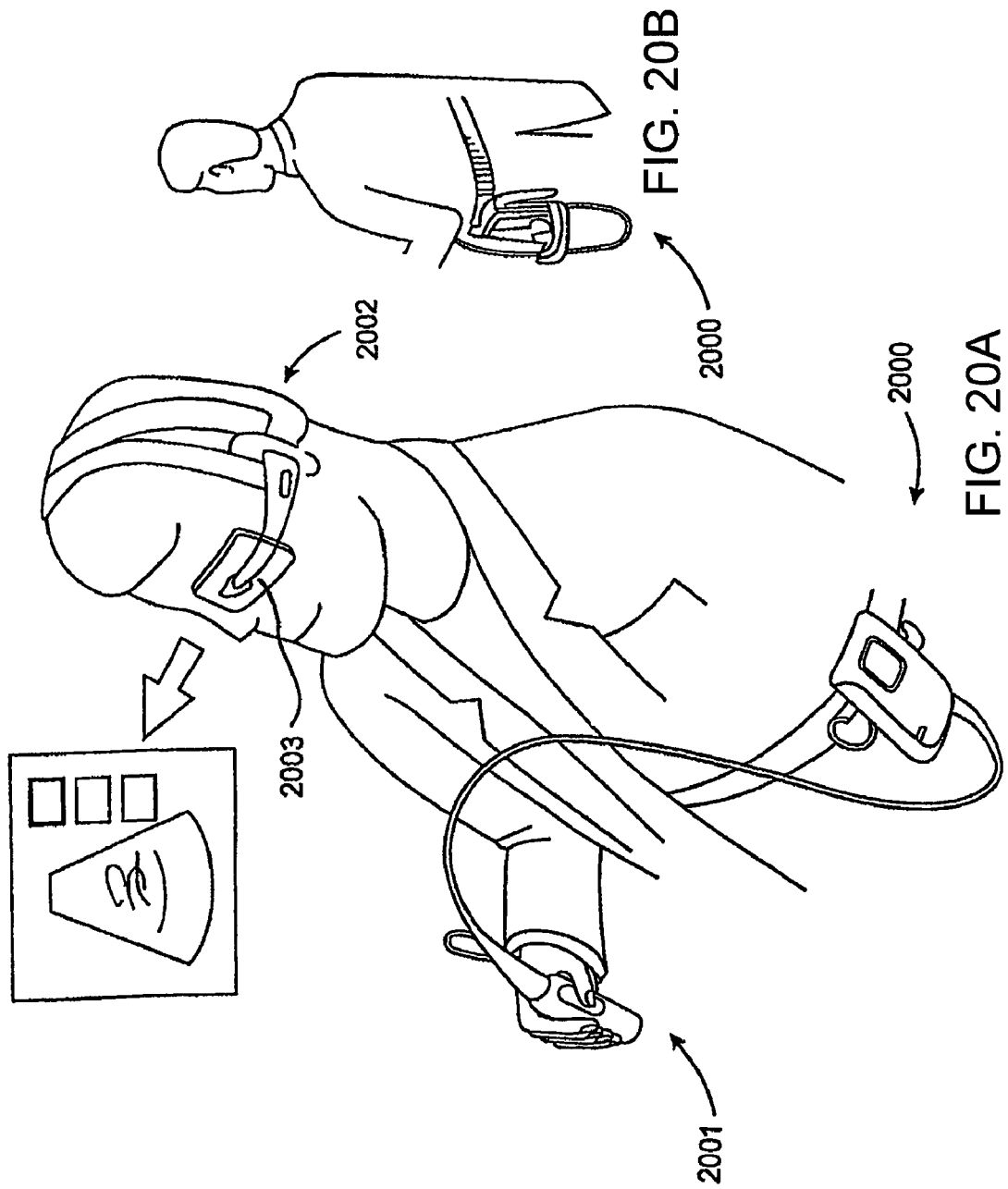

BALANCE BODY ULTRASOUND SYSTEM

CROSS-REFERENCE TO RELATED APPLICATIONS

This application is a continuation of U.S. application Ser. No. 10/099,474, filed Mar. 15, 2002; which is a continuation-in-part of U.S. application Ser. No. 10/062,179, filed Feb. 1, 2002, now U.S. Pat. No. 6,962,566; which is a continuation of U.S. application Ser. No. 09/840,002, filed Apr. 19, 2001, now U.S. Pat. No. 6,569,101; and U.S. application Ser. No. 10/099,474 is also a continuation-in-part of U.S. application Ser. No. 09/630,165, filed Aug. 1, 2000, now U.S. Pat. No. 6,416,475; which is a continuation-in-part of U.S. application Ser. No. 09/167,964, filed Oct. 6, 1998, now U.S. Pat. No. 6,135,961; which is a continuation-in-part of U.S. application Ser. No. 08/863,937, filed May 27, 1997, now U.S. Pat. No. 5,817,024; and U.S. application Ser. No. 09/167,964 is also a continuation-in-part of U.S. application Ser. No. 08/826,543, filed Apr. 3, 1997, now U.S. Pat. No. 5,893,363; which is a continuation-in-part of U.S. application Ser. No. 08/672,782, filed Jun. 28, 1996, now U.S. Pat. No. 5,722,412; and U.S. patent application Ser. No. 08/863,937 is a continuation-in-part of U.S. application Ser. No. 08/672,782, filed Jun. 28, 1996, now U.S. Pat. No. 5,722,412, the full disclosures of which are all incorporated herein by reference.

TECHNICAL FIELD

This invention relates to handheld ultrasound instruments having various diagnostic modes and transducer assemblies incorporating a balance body design, or other form factor to reduce strain of use during scanning procedures.

BACKGROUND OF THE INVENTION

As is well known, modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by SonoSite, Inc., assignee of the present invention, were smaller, desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

However, with the ever increasing density of digital electronics, it is now possible to foresee a time when ultrasound systems will be able to be miniaturized to a size even smaller than their much earlier ancestors. The physician is accustomed to working with a hand held ultrasonic scanhead that is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

The tendency has been the smaller systems also lose attributes of their larger, stationary cousins due to limitations in space and power availability, the same factors that increase portability. An inverse relation exists between size and feature set. The use of digital beamformers and digital signal processing has allowed the expansion of capabilities of the smaller, more portable ultrasound systems relative to their predecessors. Recent releases of product like the SonoSite 180 have demonstrated the ability of manufacturers to reduce the size and weight of an ultrasound system while still delivering acceptable performance. As technology improves in both digital signal processing and power management, there remains a need for providing a hand held or portable ultrasound system that delivers acceptable performance characteristics, and at the same time is easy to use. There also remains a need for providing a method of being able to reduce costs to the users of ultrasound systems by providing an affordable and easily obtainable upgrade path to such user friendly ultrasound systems, both for hardware elements, and software.

BRIEF SUMMARY OF THE INVENTION

The present invention relates to hand held ultrasonic systems providing the advances of digital signal processing and advanced human factors usability. The various design elements of the ultrasound systems presented herein are based on a series of common system electronics detailed in previously listed co-pending applications.

At its heart, the present invention provides a hand held ultrasound system having a balance body, a transducer assembly connected to said balance body via a communication means and a plurality of control elements arranged in an ergonomic fashion on said balance body, such that a user may hold said system and operate at least one of said control elements with the same hand.

In a second embodiment of the present invention, a medical ultrasound system comprising a balance body incorporating system electronics, a power supply and a user interface wherein said user interface comprises a D-controller and a touch screen and a transducer assembly attached to said balanced body via a cable. Control of the medical ultrasound device is achieved through selecting through a series of window menus either by using the D-controller or the touch screen or a combination of both. The second embodiment is lightweight and preferably weighs less than three and a half pounds (3.50 lbs.) and the balance body can be held with the same hand that operates the D-controller. Optionally the system further comprises an I/O port for connecting to a docking station, and a handle.

In a third embodiment, we describe a lightweight diagnostic ultrasound instrument comprising a body having a power supply, a user interface for controlling the instrument, a display screen, and a system electronics package capable of a plurality of diagnostic ultrasound modes, said body weighting less than three pounds; a transducer assembly comprising a digital beam former, an A/D converter circuit, and a transducer array, the transducer assembly weighing less than one pound; and a wire connecting said body and said transducer assembly, the wire having a path for feeding power from the power supply to the transducer assembly, and a signal path for transmitting digital signals between the system electronics and the transducer assembly.

In a fourth embodiment we describe a wireless diagnostic ultrasound system comprising; a first body having system electronics, a user interface having a display screen and at least one control element, a first wireless transmit/receive element and a first power supply, said first body weighing less than two pounds; and a second body having a digital beam former, an A/D converter circuit, a transducer array, a second power supply, and a second transmit/receive element such that the digital beam former can be controlled by the system electronics via the first and second transmit/receive elements, said second body weighing less than one pound.

In still another embodiment, we describe a lightweight medical ultrasound system comprising a first body having system electronics, a first transmit/receive element and a first power supply, said first body weighing less than two pounds; a second body having a digital beam former; an A/D converter circuit, a transducer array, a second power supply, a second transmit/receive element and at least one control element, said second body weighing less than one pound; and a headset comprising a visual display, a receive element and a third power supply such that the first body, second body and head set are in communication with each other through the first and second transmit/receive element and the receive element so that a user may control the system through the at least one control element of the second body, while the first body performs the diagnostic operations through said system electronics, and the user may see the operations through the visual display of the head set.

In yet another embodiment, we describe a system as detailed above wherein the first body and the second body are incorporated into a single transducer assembly weighing less than two pounds and sharing a single power supply and having a single transmit/receive element.

Methods of using the various embodiments are also provided.

These and other embodiments of the present invention will become readily apparent upon a detailed inspection of the detailed description of the invention, and a study of the appended claims.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIGS. 2-20B illustrate alternative embodiments of the present invention.

DETAILED DESCRIPTION OF THE INVENTION

Several terms have been clarified here to facilitate an understanding of the present invention.

Balance Body: A design for an ultrasound device where the center of gravity for the device is positioned close to the strength of a user's hand. By shifting components around in the internal arrangement of the device, an aperture can be made in the device body where system electronics and other essential elements are, such that the device body is balanced for more comfortable holding in a user's hand.

D-controller: Any of a variety of control devices allowing a user to "point and click." The D-controller may be a digital directional controller (such as a four or eight directional controller), an analog "joystick." The D-controller allows a user to navigate an on-screen menu or displayed graphics similar to the use of a touch pad or lap top "nipple" pointing style device.

The present invention describes a hand held ultrasound system having a balance body, a transducer assembly connected to said balance body via a connection means, and a plurality of control elements arranged in an ergonomic fashion on the balance body. The system is designed such that a user may hold the balance body and operate a key control element, such as a D-controller, with the same hand.

Figure 1A:
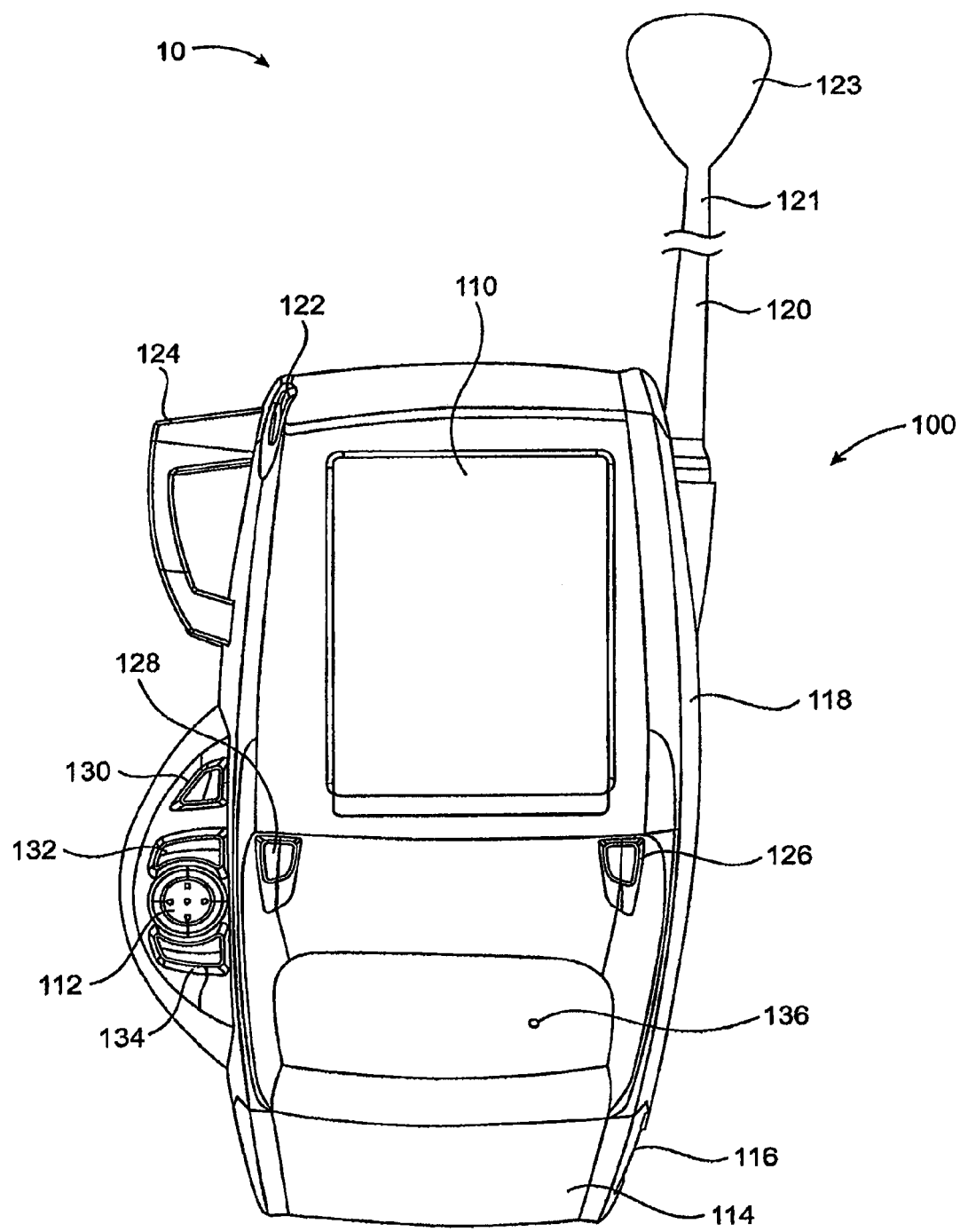
FIGS. 1A-D illustrate a balance body ultrasound device of the present invention.
Figure 1B:
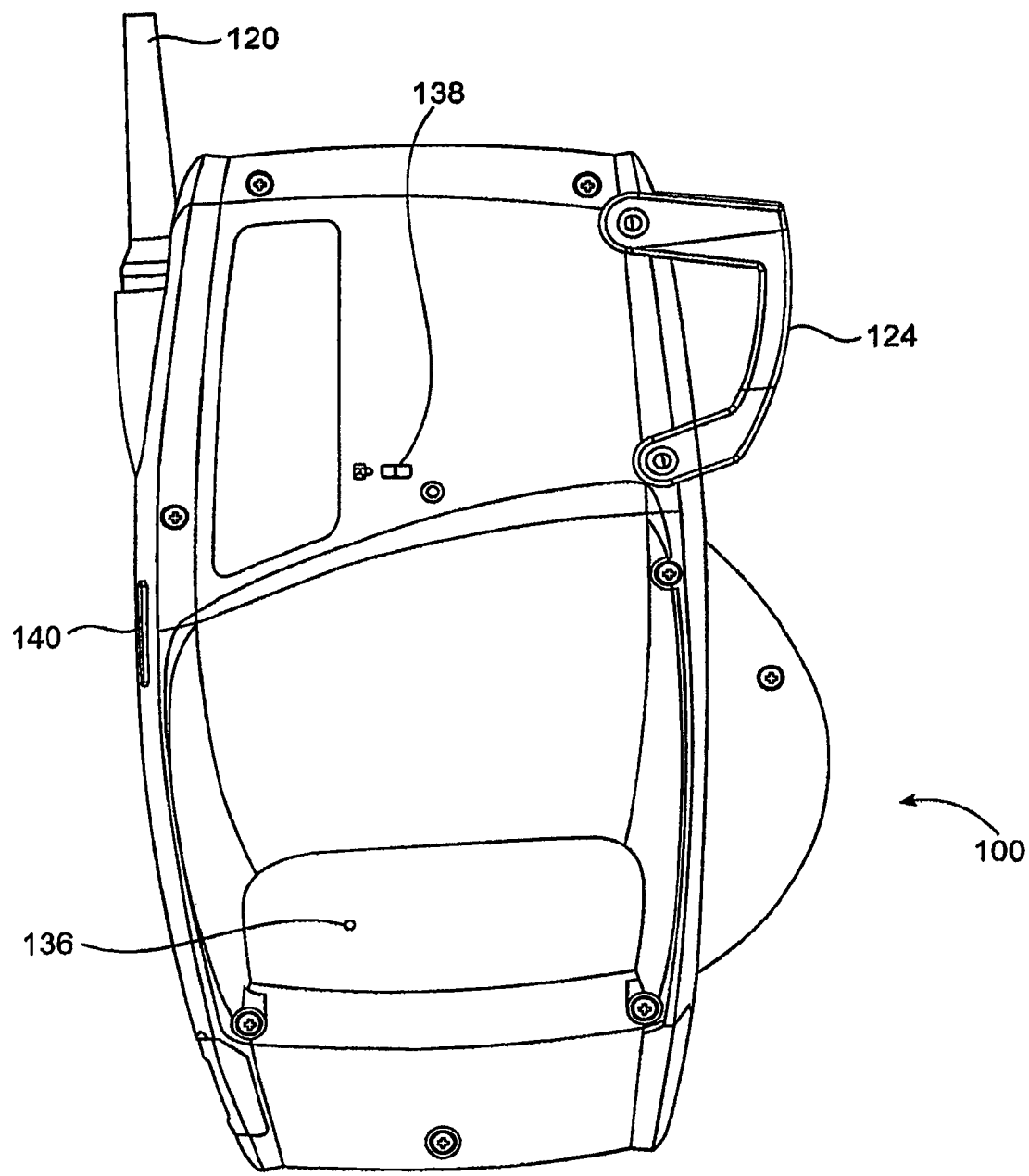
Figure 1C:
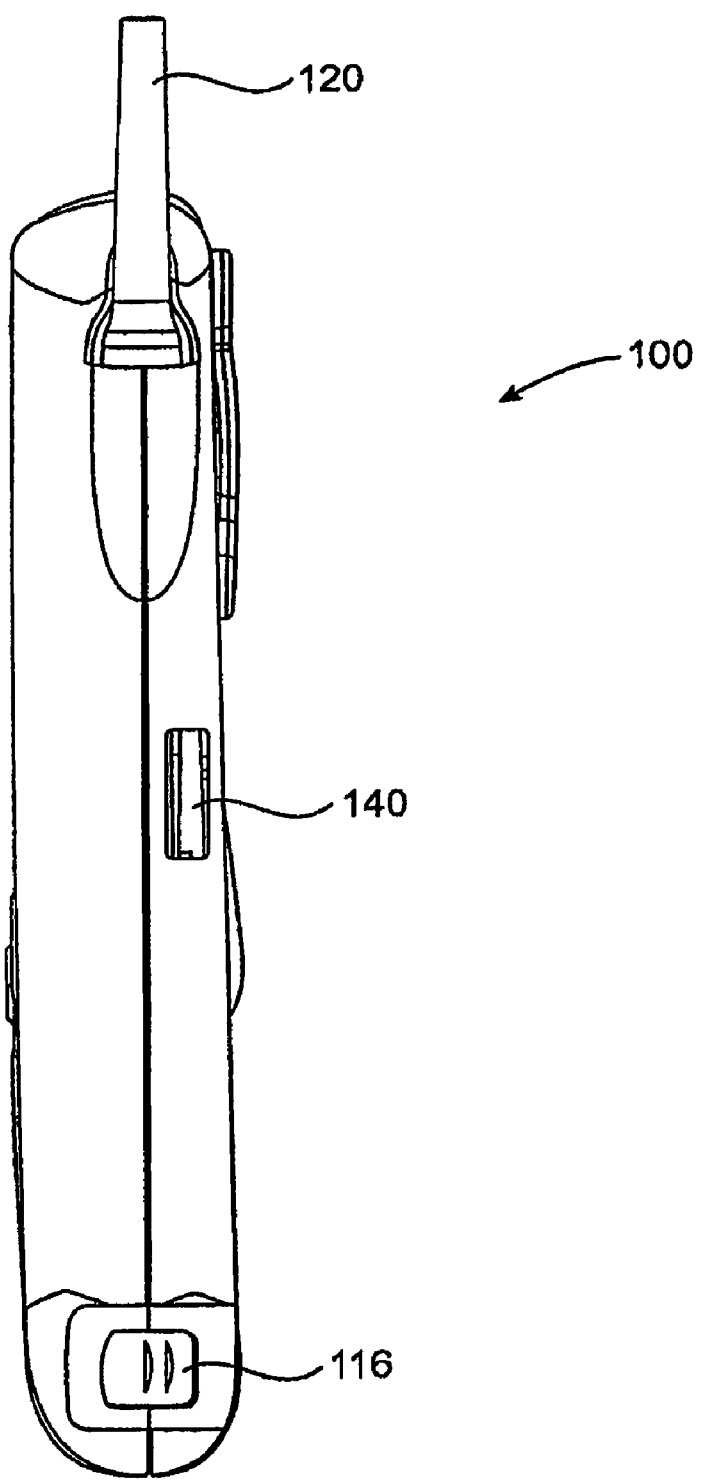

Turning now to FIGS. 1A-1C, a medical ultrasound system 10 comprises a balance body 100 incorporating system electronics, a power supply and a user interface wherein the user interface comprises a D-controller 112 and a touch screen 110, the transducer assembly 123 is connected to the balance body 100 via a cable 121 extending from a cable port 120.

The balance body 100 is a housing containing the system electronics, power supply and user interface. The balance body 100 has an aperture 136 through which a user may insert his or her hand. The aperture 136 is shaped to be comfortable for the majority of users. The balance body 100 has the aperture 136 for the user's hand arranged so the user's palm and fingers support the weight of the device by being essentially flat against the backside of the balance body 100. The user's thumb wraps around to the front face of the balance body 100, and the D-controller 112 is positioned such that the user's thumb can easily manipulate the D-controller 112 while the user's palm and fingers support the weight of the balance body. In one embodiment, the power supply is located in the handle 114, opposite the system electronics (the aperture for a user's hand being between the power supply and the system electronics). Since the power supply is one of the heavier elements of the medical ultrasound system 10, the counter balancing effect makes the medical ultrasound system 10 easier to use and hold through the aperture 136. A power supply release button 116 is provided when necessary to remove the power supply within the handle 114.

A plurality of control elements or buttons 128, 132, 134 are also accessible to the user's thumb, these control buttons or control elements are arrayed about the D-controller 112 so the user does not have to extend the thumb into an awkward position in order to actuate these control elements. Additional control elements 130, 126, such as the on/off switch 126 are purposefully positioned out of reach of the user's thumb, thus avoiding inadvertently turning the system off during a medical scan. The control elements need not be buttons per se. The present invention can also operate using a series of touch pads that would supplement the primary D-controller 112, or utilize spring loaded dials that may be adjusted, then depressed below the surface of the balance body. The screen 110 is preferably a touch screen, and a stylus 122 is incorporated into the balance body 100 so a user may use the stylus 122, fingers (of the user's second hand), or the D-controller 112 to input information through the touch screen 110. It should be noted here the D-controller 112 can also be used to position a pointer in a graphics image. In this manner a user may select an area of an image for enhanced viewing, or gain additional information about an icon on the screen or data about a scan image, or perform a manual trace of a scan image. The touch screen 110 has a plurality of image presentation styles, and among them is a QWERTY style keyboard so a user can input information such as patient data, or notes from an ultrasound scan.

The transducer assembly 123, or scan head comprises a transducer array and an inter-connector for coupling the transducer array to the cable. The transducer assembly 123 is connected to the balance body 100 by a cable 121 that feeds control signals to the transducer array (for steering, scan mode, etc.) as well as power from the power supply in the balance body 100. The transducer assembly 123 may be permanently affixed to the balance body through the cable 121, or the cable may be removable such that a different scan head/transducer assembly can be attached to the balance body.

Additional features that may be incorporated onto the balance body include a holster 124 for retaining the transducer assembly 123 when not in use, a receptacle for placement of the stylus, an aperture 138 on the back side for connecting a locking pin into the balance body (when placed into a docking station), a spacer (not shown) for use in the aperture to accommodate smaller user hands and increase the user audience able to use the system and a hinge for the display screen so it can be tilted or swiveled. A data I/O port 140 is provided for communication with a docking station. Referring to FIGS. 7A & 7B, a balance body 700 is shown before (FIG. 7A) and after (FIG. 7B) insertion into a docking station 701. U.S. Pat. No. 6,416,475 teaches a PCMCIA data I/O port.

Dimensionally, the medical ultrasound system of the present embodiment ha a total system weight under three and one half pounds (3.50 lbs.). The cable is of varying length but is designed to be sufficient for a user to comfortably hold the balance body in the user's field of view and scan a patient simultaneously. The balance body comprises the bulk of the weight while the transducer assembly generally weighs less than eight ounces (0.5 lbs.). The balance body measures less than twelve inches long, seven inches in height and two inches in depth (12"×7"×2") not including the transducer assembly and attaching cable.

Figure 1D:
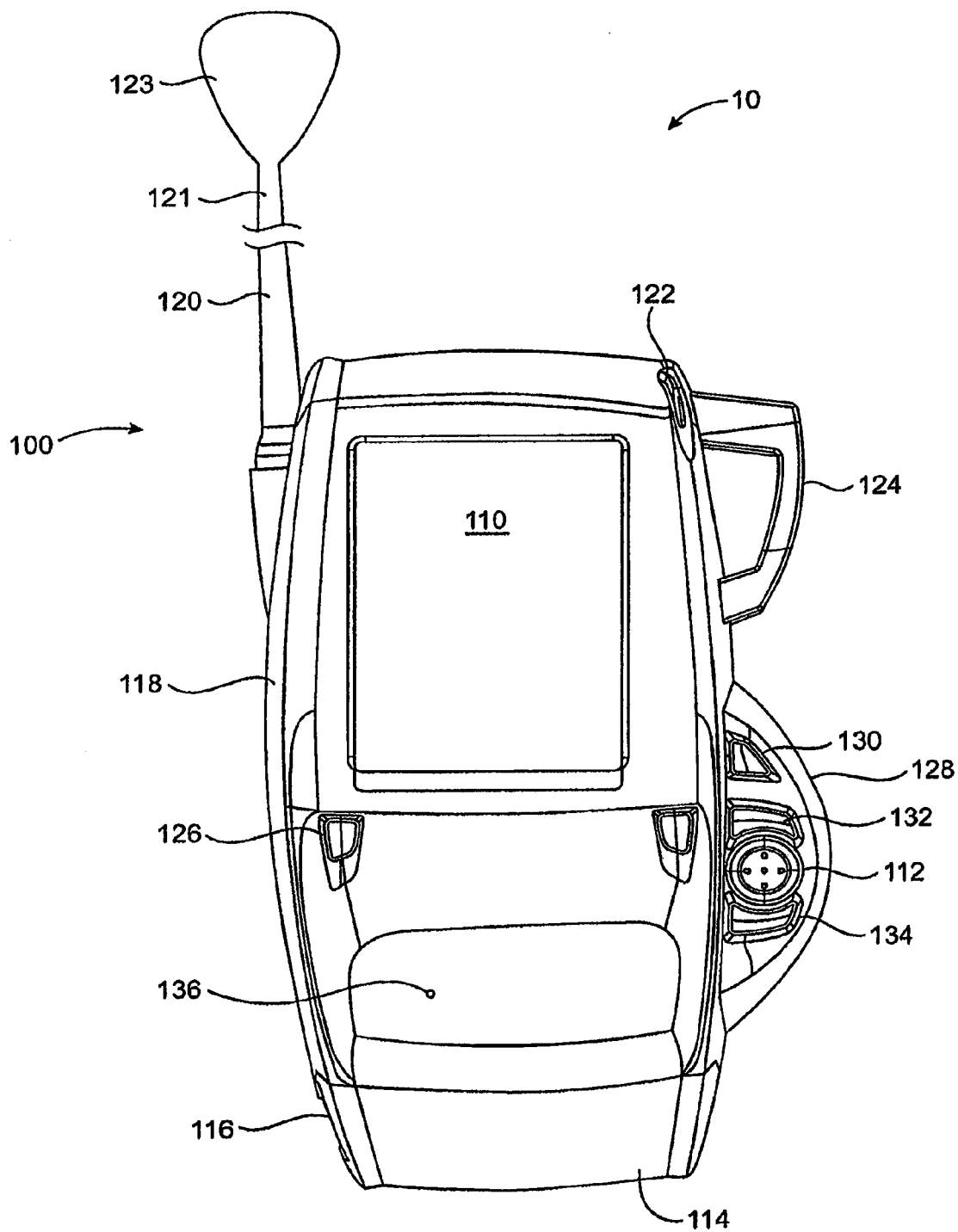
Figure 2:
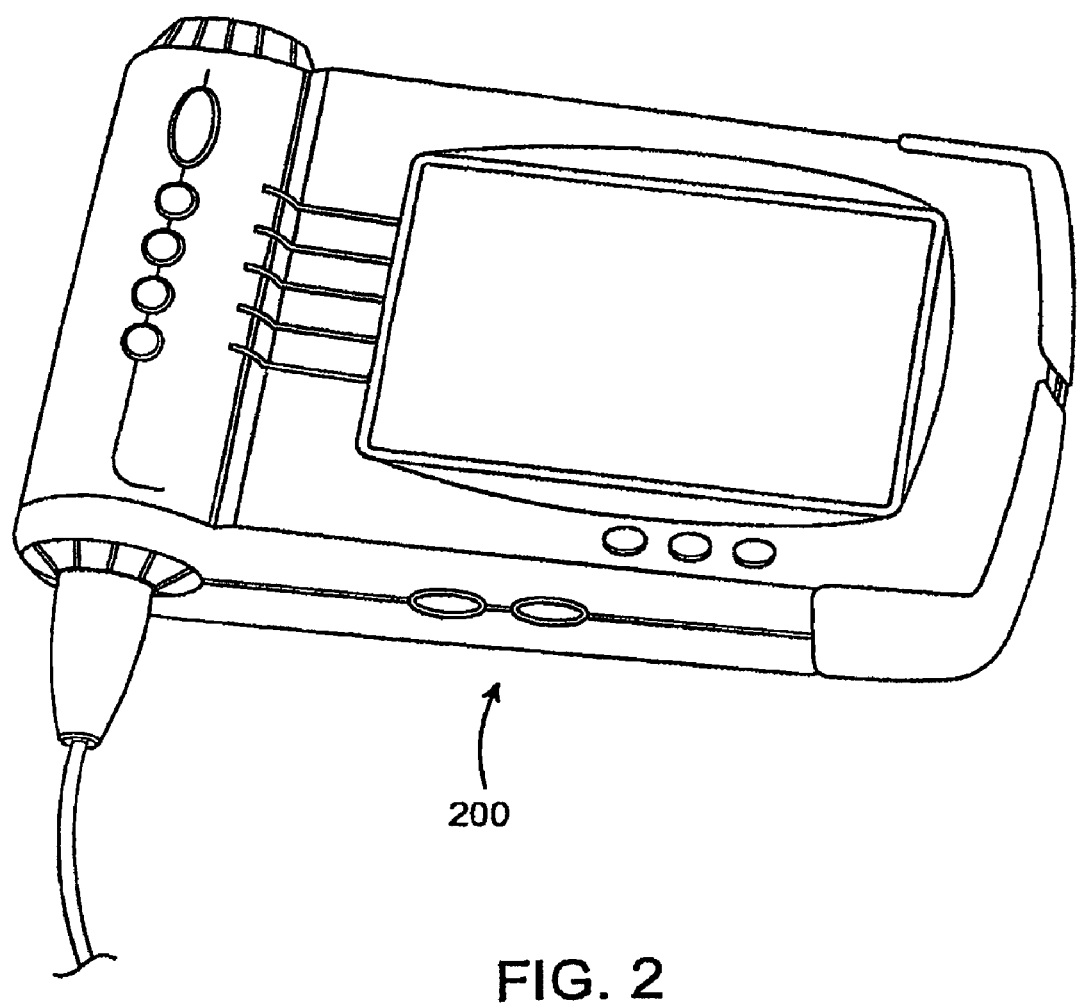
Figure 3:
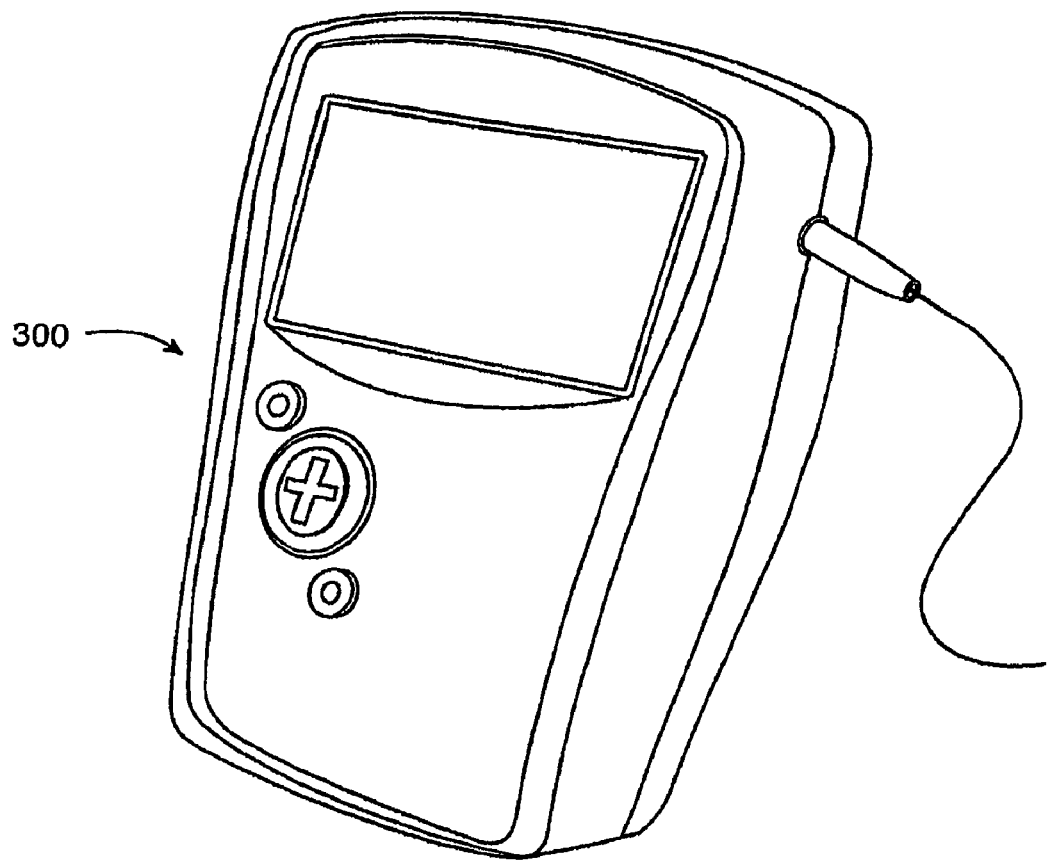
Figure 4:
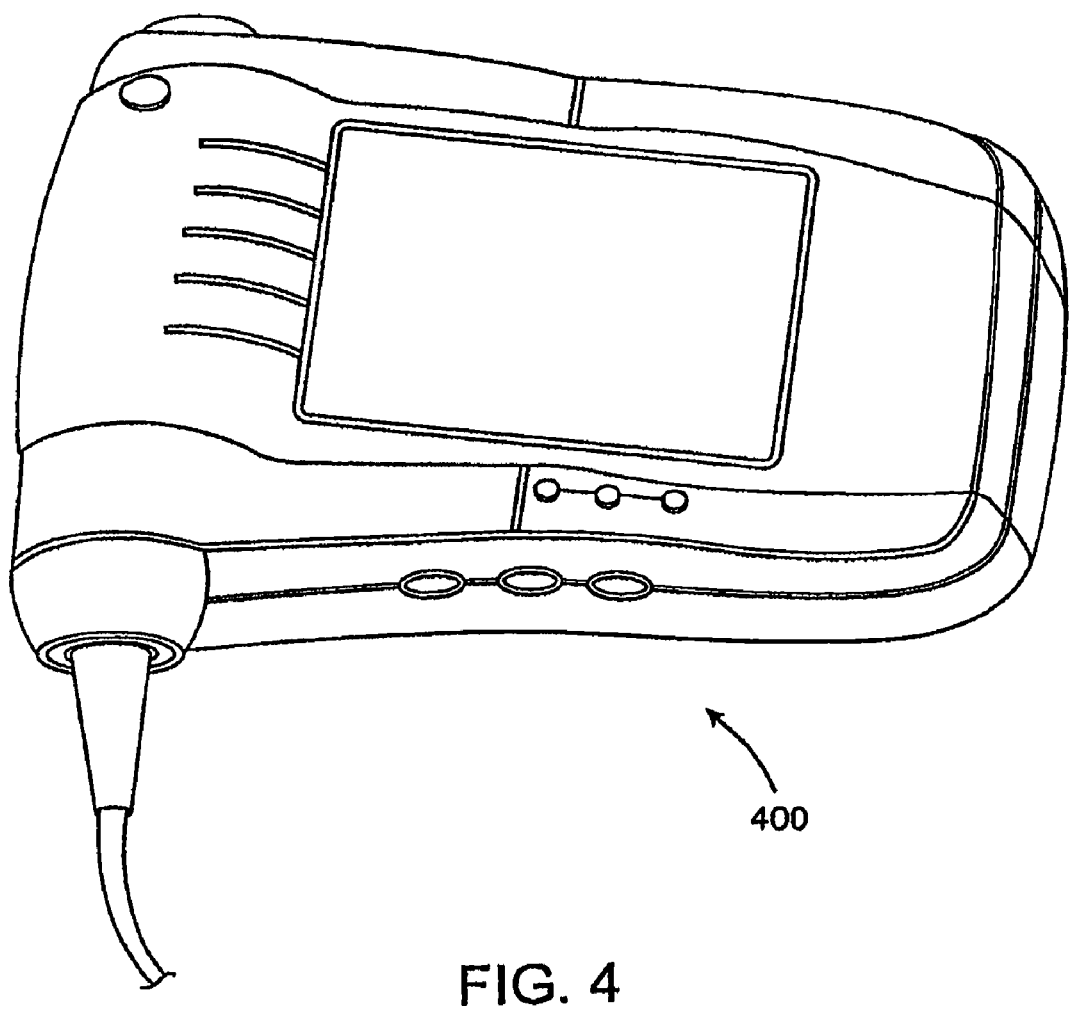
Figure 5:
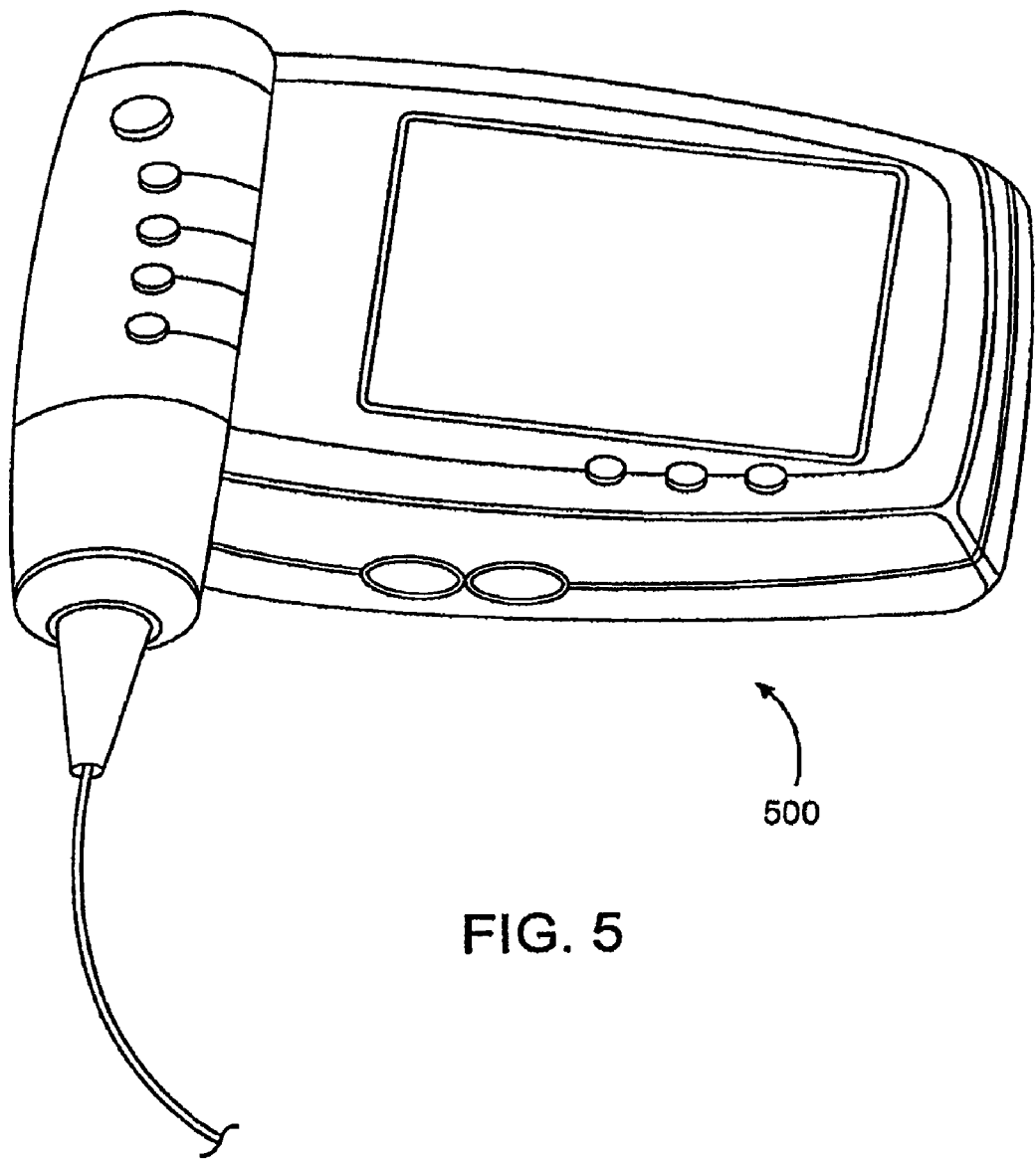
Figure 6:
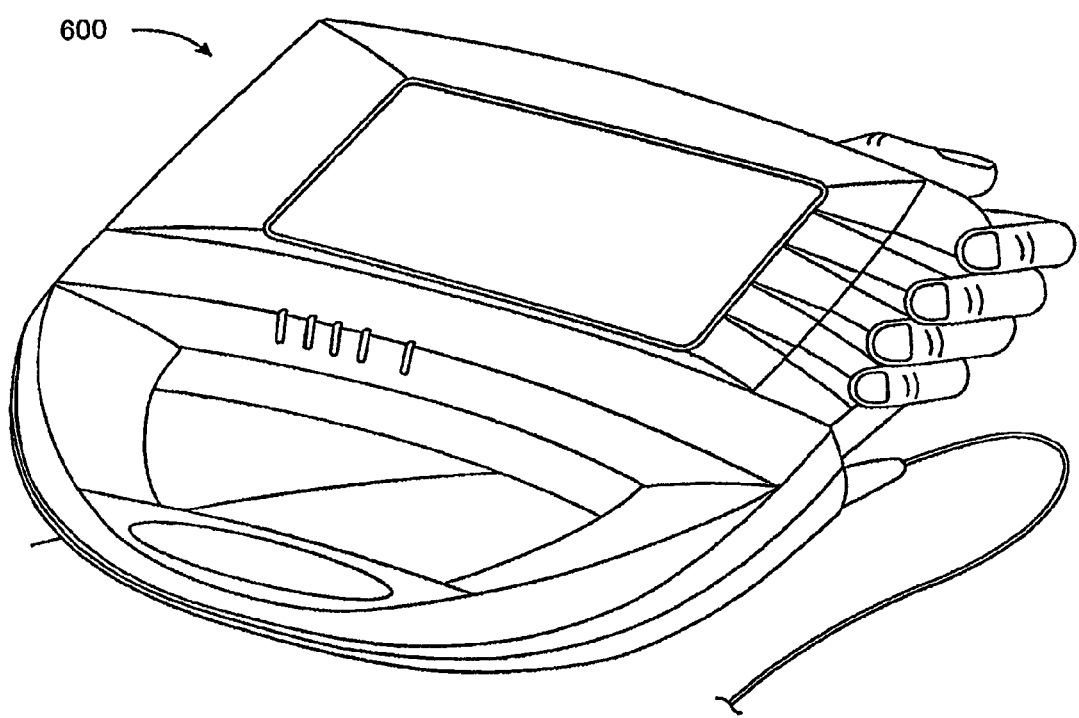
Figure 8:
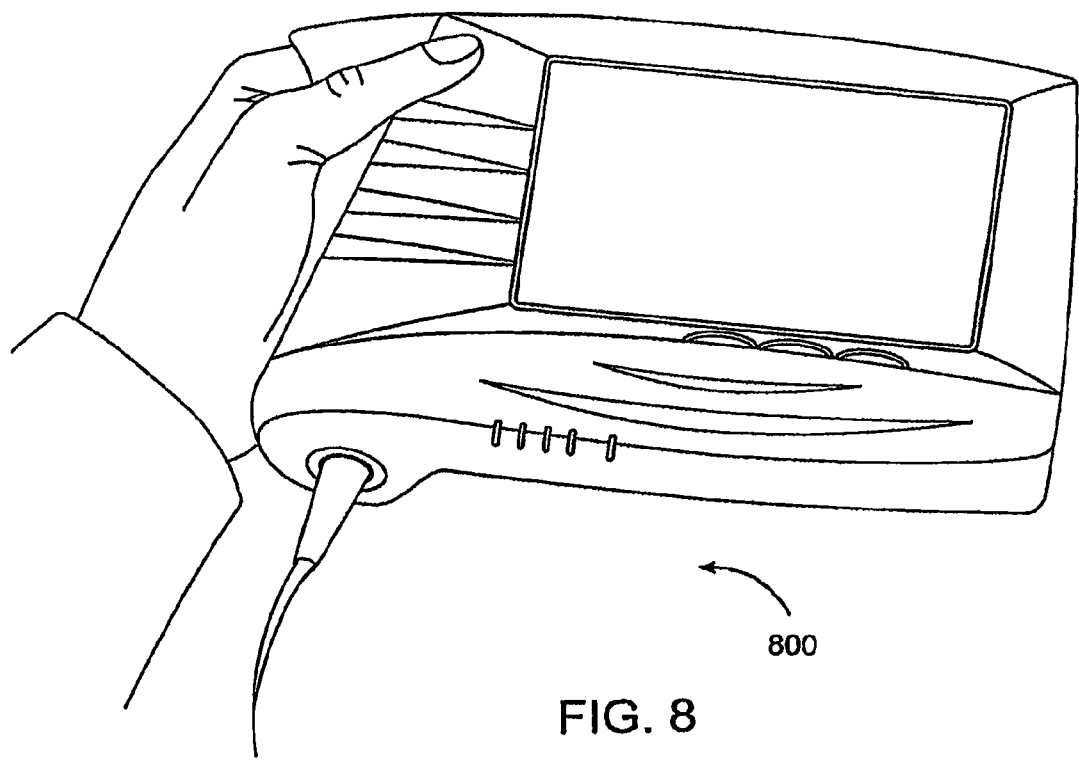
Figure 9:
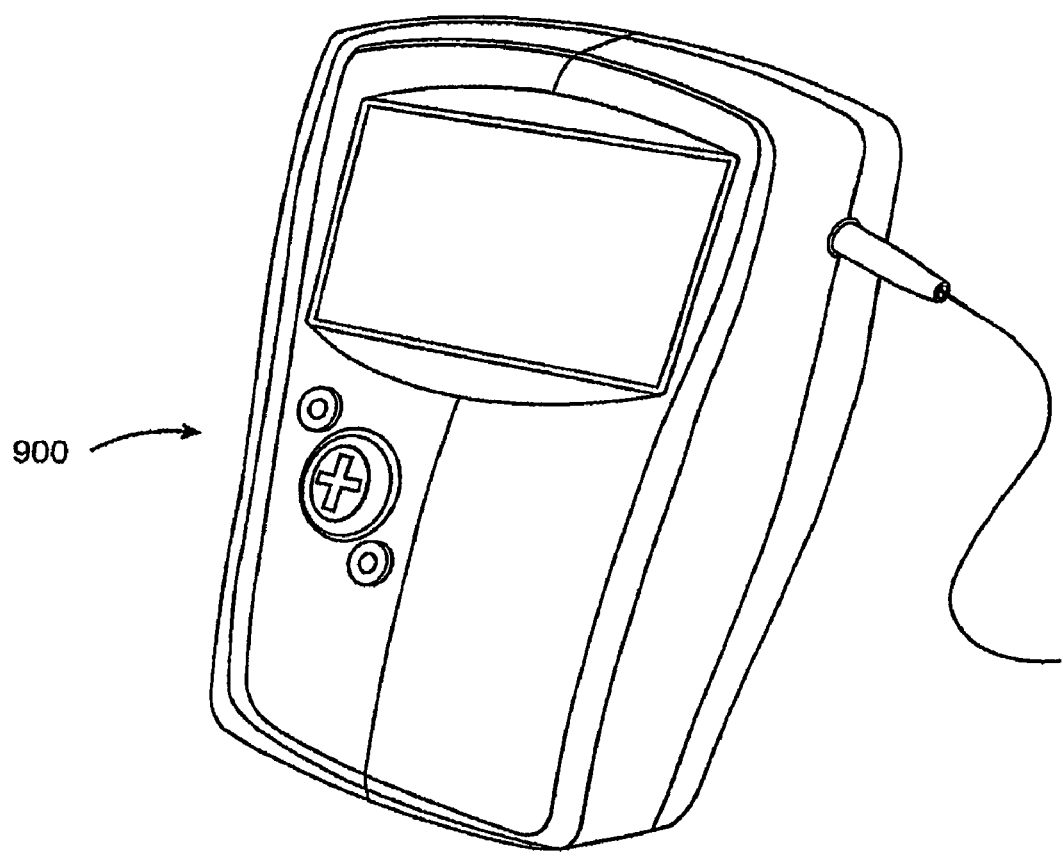
Figure 10:
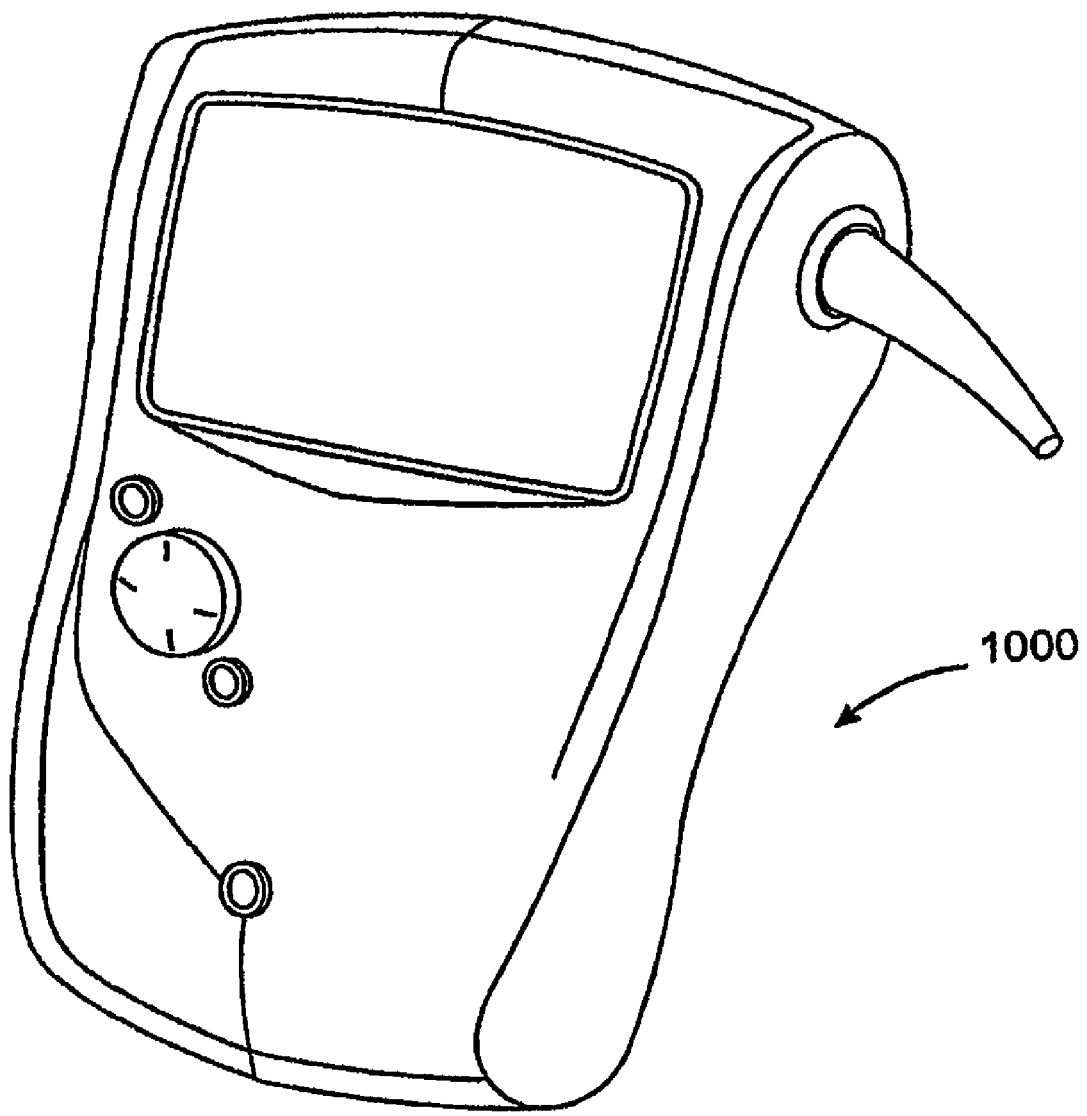
Figure 11:
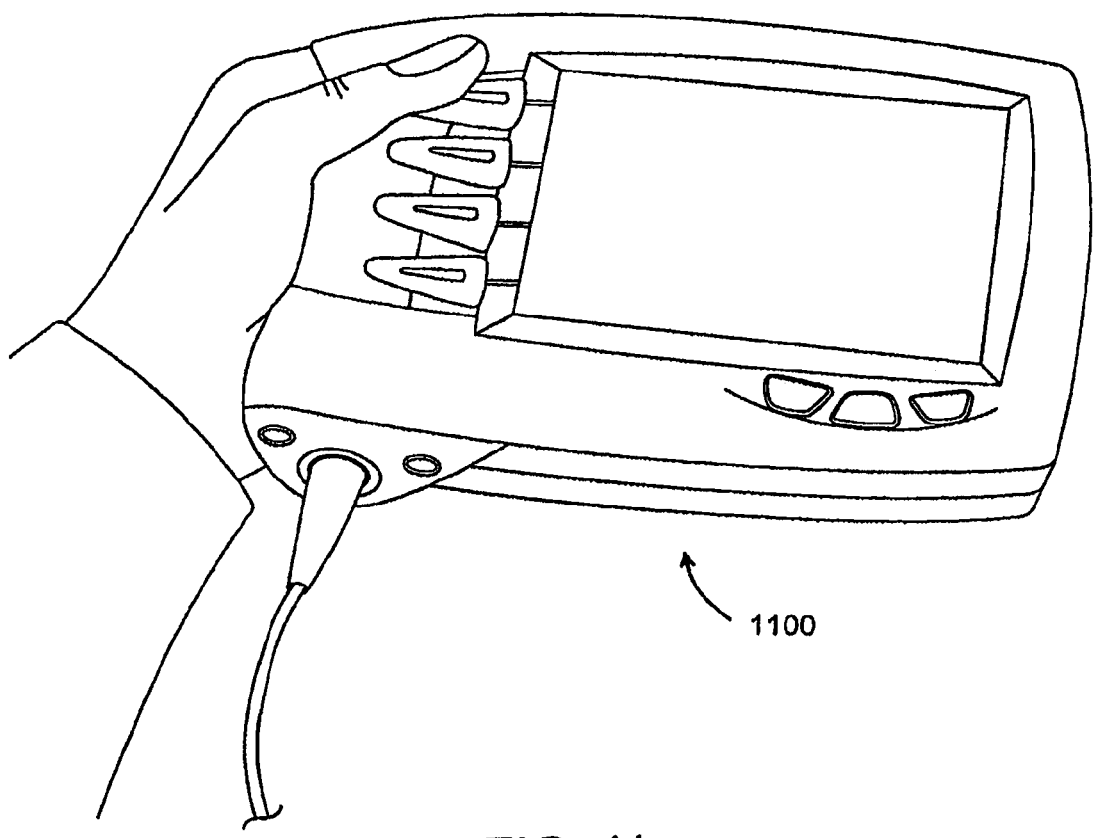
Figure 12:
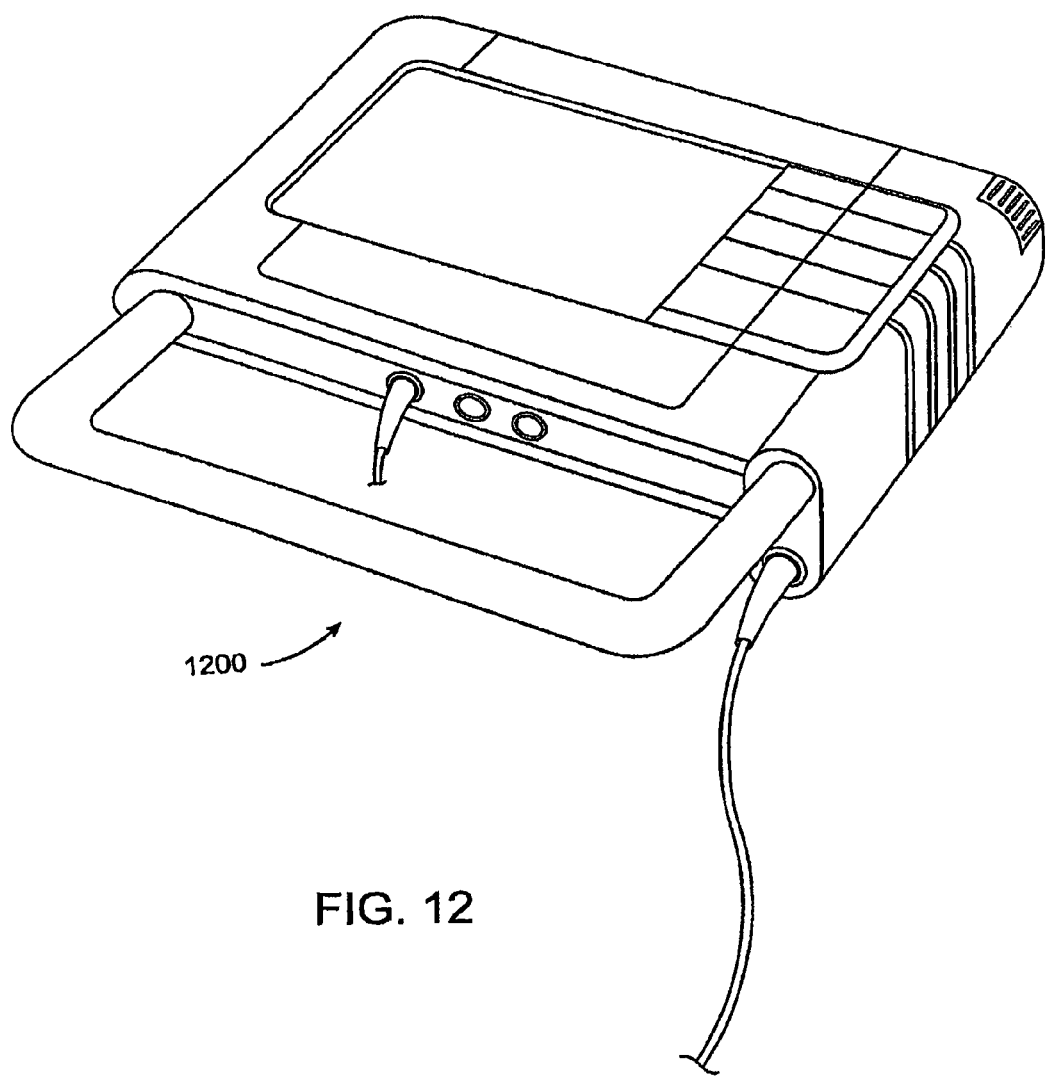
Figures 13A, 13B:
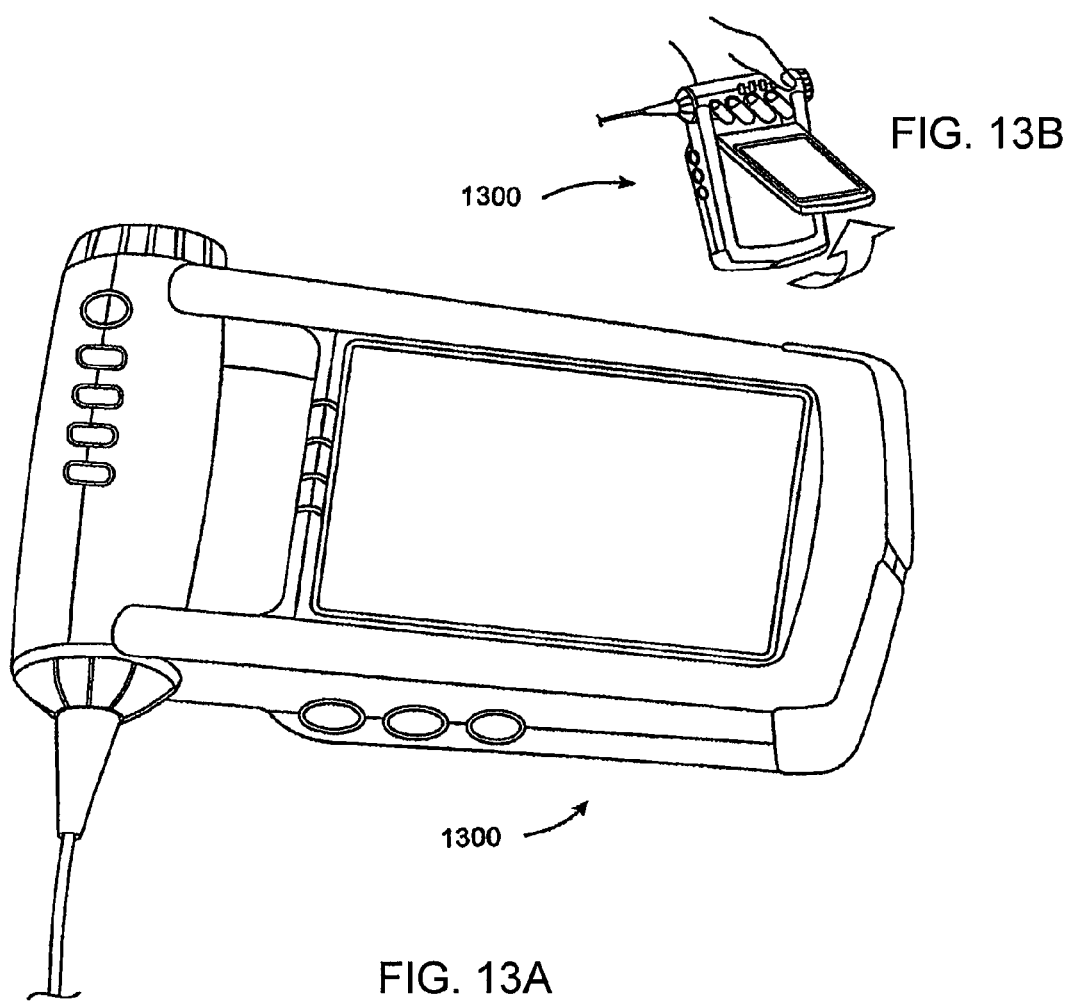
Figures 14A, 14B:
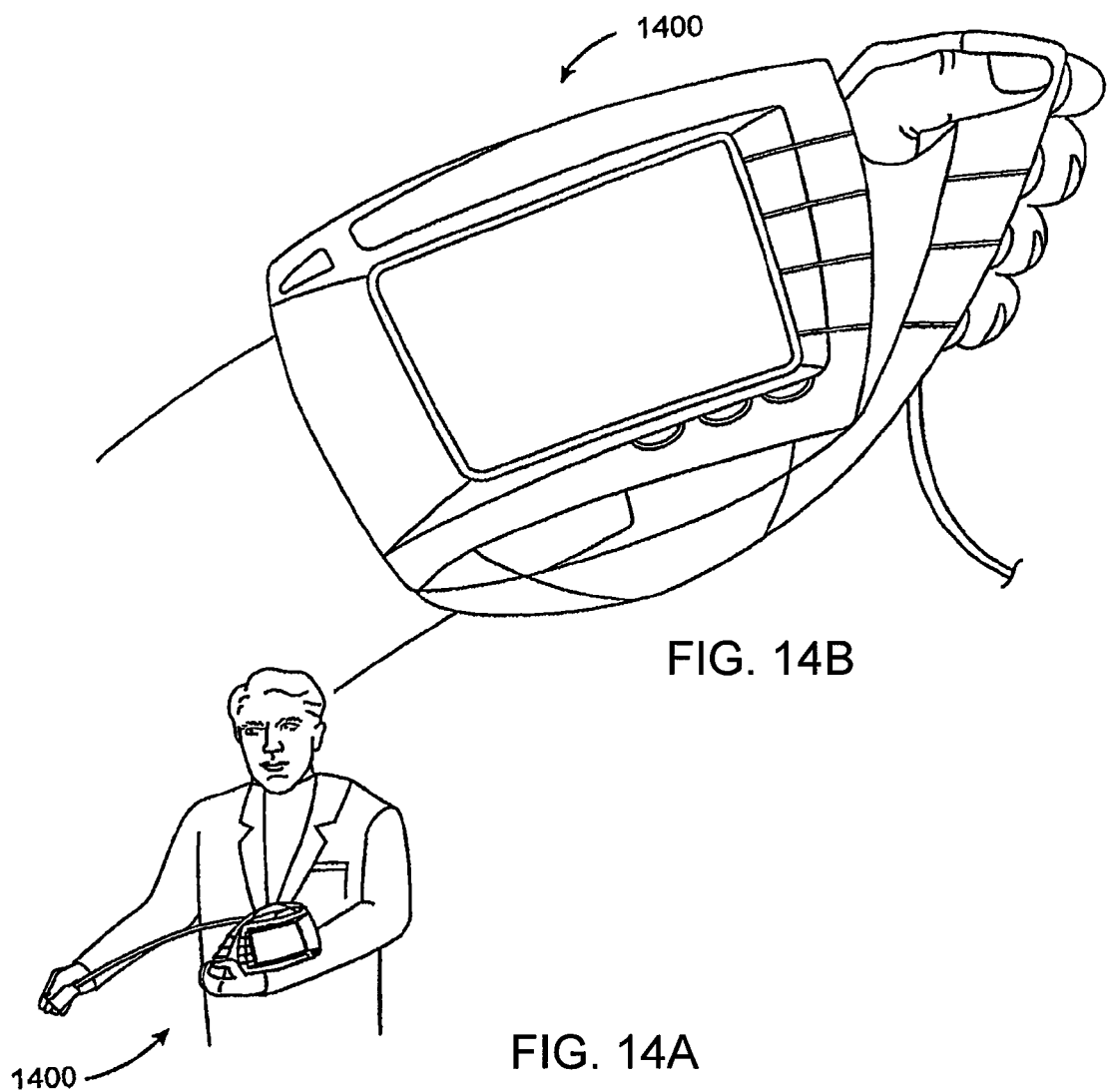
Figures 15A, 15B:
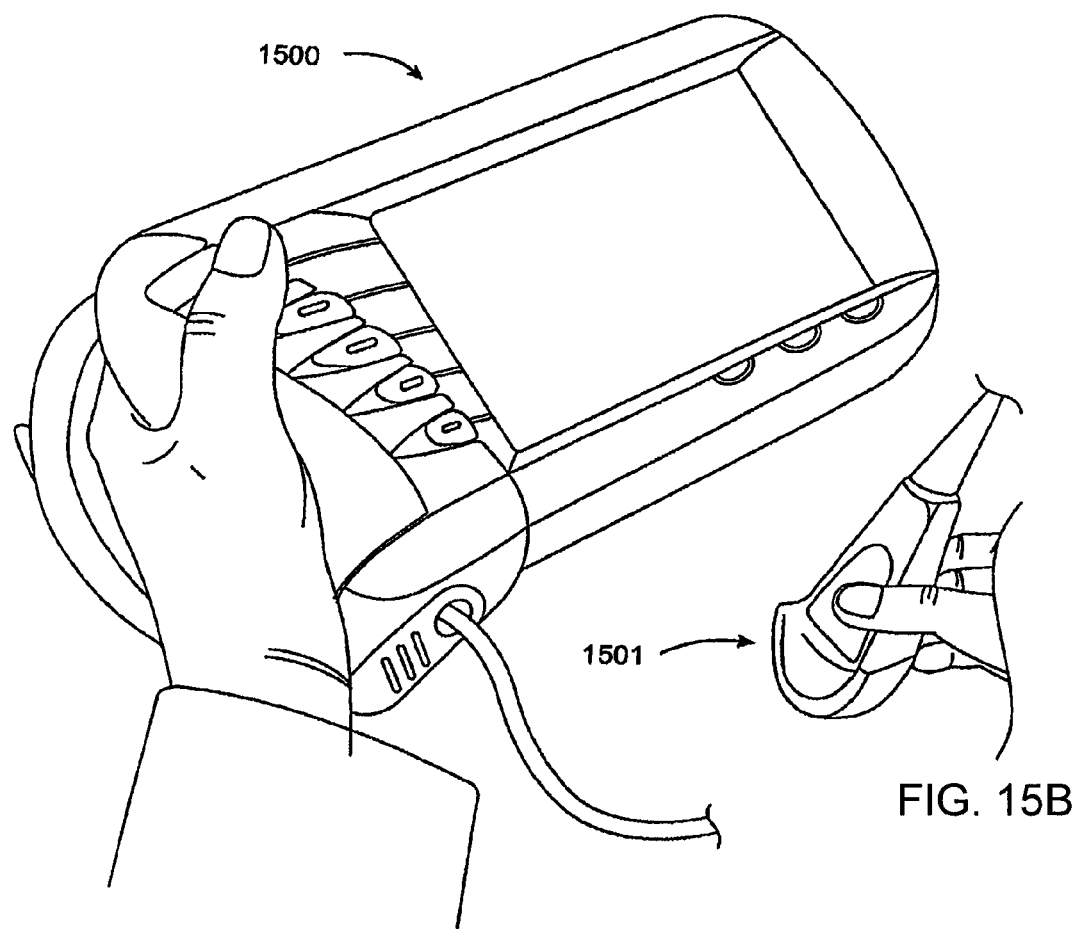
Figure 17:
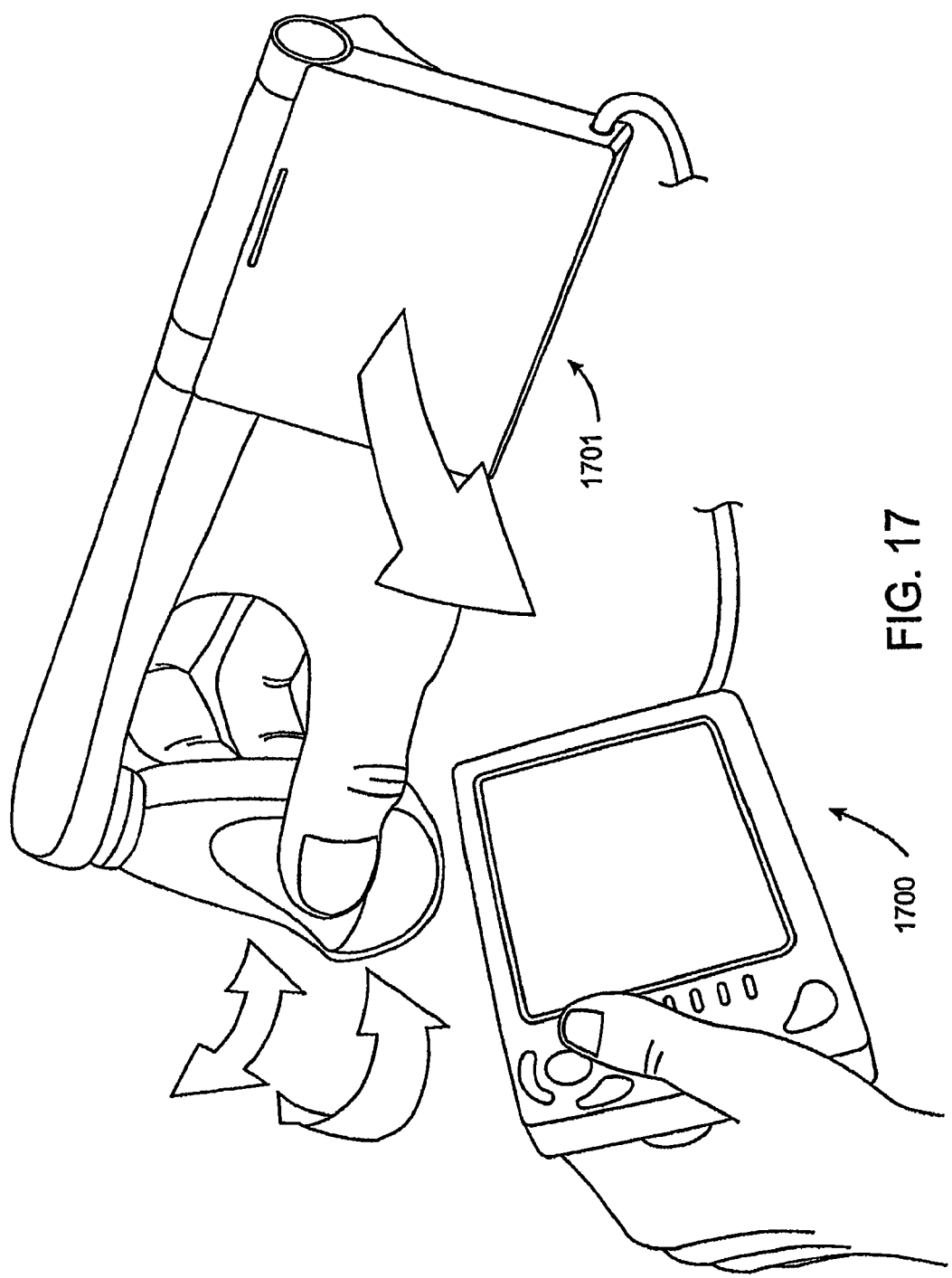

FIG. 1D illustrates a right-handed model of the present invention, where the controls are a mirror image of those in FIGS. 1A-C. FIGS. 2-6 and 8-17 show lightweight ultrasound instrument bodies (200, 300, 400, 500, 600, 800, 900, 1000, 1100, 1200, 1300, 1400, 1500, 1600, 1700). FIGS. 13A and 13B show an instrument body 1300 with an adjustable display screen. FIGS. 15A, 15B and 17 show an instrument body 1500, 1700 with a transducer 1501, 1701. FIGS. 18A and 18B show an instrument body 1800 having an integrated transducer assembly.

The medical ultrasound system also allows for the entry of a key code to permit upgrades to the software of the device. The operation of the key code is explained in greater detail in co-pending U.S. application Ser. No. 10/062,179 filed Feb. 1, 2002, now U.S. Pat. No. 6,962,566.

A second embodiment of the present invention forms a lightweight ultrasound instrument comprising a body having a power supply, a user interface for controlling the instrument, a display screen, and a system electronics package capable of a plurality of diagnostic ultrasound modes. In this embodiment, the body may optionally be a balance body. A transducer assembly is attached to the body via a wire of thin flexible cable, the transducer assembly comprises a digital beam former, an A/D converter circuit and a transducer array. The body, transducer assembly and wire combined weigh less than three pounds.

The wire connecting the body and transducer assembly provides power to the transducer assembly, and a signal path for the body and transducer assembly to communicate using digital data. In this manner the need for an analog cable, having many data paths for analog signals, is eliminated, and spares additional weight. The signal from the transducer array returns through the digital beam former incorporated into the transducer assembly so only digital information goes between the body and the transducer assembly.

The control elements of the lightweight ultrasound instrument are similar to those described above. A plurality of control elements, of which one is preferably a D-controller, and a touch screen. Again the body can be held with one hand, so the user's thumb, or fingers can access the D-controller on the body.

In a third embodiment, a wireless diagnostic ultrasound system comprises a first body, and a second body. The first body is the main unit having system electronics, a user interface having a display screen and at least one control element, a first wireless transmit/receive circuit and a first power supply. The second body is a transducer assembly having a digital beam former, an A/D converter circuit, a transducer array, a second power supply and a second transmit/receive element such that the digital beam former of the second body can be controlled by the system electronics of the first body using the first and second transmit/receive circuits. The first and second transmit/receive circuits being a wireless means for communicating between the first body and the second body. Wireless data transfer and communication are well-understood technologies. Any standard wireless transmission standard capable of supporting the digital information communication of the present invention may be used.

The display screen in this embodiment is preferably a touch screen as well. The use of touch screen permits the same advantages for ease of use to a user as previously described. A D-controller as one of the control elements allows for simple one-handed operation of the first body while the second hand holds the transducer assembly in place. The wireless design permits a user total freedom from encumbering cable and wire connections to the first body such that the transducer array can be positioned easily for manual steering.

In a fourth embodiment, the invention comprises a first body having system electronics (FIGS. 2A and 20B at 2000), a first transmit and receive element (FIG. 20A at 2001), and a first power supply. The first body weighs less than two pounds. A second body houses the transducer assembly. The transducer assembly has a digital beam former, an A/D circuit, a transducer array, a second power supply, a second transmit and receive element and at least one control element. The second body weighs less than one pound. A head set (FIG. 20A at 2002) is provided comprising a visual display (FIG. 20A at 2003), a receive element and a third power supply such that the first body, second body and head set are all in real time communication with each other. U.S. Pat. No. 5,817,024 describes that video information can be communicated from a video output in several television formats. The user can control the system through the second body or first body while visualizing the ultrasound scan through the head set. Voice recognition capability can be added to the head set through a head set microphone, allowing a user to command the operation of the ultrasound system at some level using voice activated commands instead of one or more of the manual control elements. FIGS. 19A, 19B and 19C show a medical ultrasound system where the first body and the second body are incorporated into a single transducer assembly 1900. A headset 1901 communicates wirelessly with single transducer assembly 1900.

Another embodiment of the invention may comprise a medical ultrasound system wherein an I/O port for connecting to a docking station further comprises a data path, a control path, and a power path for communicating with the docking station, such that data can move between said medical ultrasound system and the docking station, such that the medical ultrasound system can be controlled through the docking station, and such that the power supply can be recharged through the power path.

Yet another embodiment of the invention may comprise a medical ultrasound system comprising a balance body incorporating system electronics, a power supply and a user interface wherein the user interface comprises a D-controller and a touch screen and a transducer assembly attached to the balanced body via a cable. In this embodiment, the system electronics comprise a digital beam former, an image processor, and a first digital signal processor capable of processing B mode, M mode and flow (2D Doppler) scans. Some embodiments may comprise a second digital signal processor comprising a digital Doppler QBP filter for filtering PW Doppler signals and a digital signal processor core for PW Doppler signal processing. A description of a digital signal processor of this type is described in U.S. Pat. No. 6,569,101, incorporated herein by reference. In some embodiments, the first digital signal processor and the second digital signal processor are integrated into a single application specific integrated circuit (ASIC). A data storage means for ultrasound scans may be included. ASIC architecture is further described in Paragraphs 15, 50-54, 57-59, 63-65, and 67 of co-pending U.S. application Ser. No. 10/062,179, incorporated herein by reference.

Other embodiments may comprise a medical ultrasound system comprising a balance body incorporating system electronics, a power supply and a user interface wherein the user interface comprises a D-controller and a touch screen and a transducer assembly attached to the balanced body via a cable, the medical ultrasound system being a programmable diagnostic ultrasound instrument having a plurality of diagnostic modes. Other transducer and balance body assemblies are described in U.S. Pat. No. 6,416,475, incorporated by reference herein. Access to the diagnostic modes is controlled through a gate flag registry, the gate flag registry capable of modification through a verification procedure utilizing a secure means for extracting hidden bits from a keycode based on one or more unique system identifiers. Keycodes are further described in co-pending U.S. application Ser. No. 10/062,179, incorporated by reference herein.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A medical ultrasound system comprising:
   a balance body, which has a center of gravity positioned close to a strength of a user's hand when the ultrasound system is held by the user, said balance body incorporating system electronics, a power supply and a user interface wherein said user interface comprises a D-controller and a touch screen; and
   a transducer assembly attached to said balanced body via a cable, wherein the system electronics comprises:
      a digital beam former, an image processor, and a first digital signal processor capable of processing B mode, M mode and flow (2D Doppler) scans; and
      a second digital signal processor comprising:
         a digital Doppler QBP filter for filtering PW Doppler signals; and
         a digital signal processor core for PW Doppler signal processing, wherein the first digital signal processor and the second digital signal processor are integrated into a single application specific integrated circuit (ASIC).

2. The medical ultrasound system as described in claim 1, wherein control of the medical ultrasound device is achieved through selecting through a series of window menus either by using the D-controller or the touch screen or a combination of both.

3. The medical ultrasound system as described in claim 1, wherein the ultrasound system weighs less than three and a half pounds (3.50 lbs.) and the balance body can be held with the same hand that operates the D-controller.

4. The medical ultrasound system as described in claim 1, wherein the touch screen responds to a series of on screen commands and is re-programmable to make one or more hot menus.

5. The medical ultrasound system as described in claim 1, wherein the touch screen further comprises a QWERTY style keypad.

6. The medical ultrasound system as described in claim 1, wherein said transducer assembly is a pen transducer.

7. The medical ultrasound system of claim 1, further comprising a handle.

8. The medical ultrasound system as described in claim 1, further comprising a holster for retaining the transducer assembly.

9. The medical ultrasound system as described in claim 1, further comprising a data storage means for ultrasound scans.

10. The medical ultrasound system as described in claim 1, wherein said balance body comprises an aperture and internal components arranged to achieve said balance body.

11. The medical ultrasound system as described in claim 1, wherein said balance body is configured so that the user's palm and fingers support the weight of said balance body by being essentially flat against a backside of said balance body.

12. The medical ultrasound system as described in claim 1, further comprising an I/O port for connecting to a docking station.

13. The medical ultrasound system as described in claim 12, wherein the I/O port still further comprises a data path, a control path, and a power path for communicating with the docking station, such that data can move between said medical ultrasound system and said docking station, such that said medical ultrasound system can be controlled through the docking station, and such that the power supply can be recharged through the power path.

14. A lightweight diagnostic ultrasound instrument comprising:
- a body having a power supply, a user interface for controlling the instrument, a display screen, and a system electronics package capable of a plurality of diagnostic ultrasound modes, said body weighing less than three pounds, wherein said user interface comprises a controller and wherein said ultrasound instrument is configured so that a user may hold said ultrasound system with one hand and operate said controller with said one hand and wherein the system electronics package comprises an image processor, and a first digital signal processor capable of processing B mode, M mode and flow (2D Doppler) scans, having a second digital signal processor comprising:
  - a digital Doppler QBP filter for filtering PW Doppler signals; and
  - a digital signal processor core for PW Doppler signal processing wherein the first digital signal processor and the second digital signal processor are integrated into a single application specific integrated circuit (ASIC);
- a transducer assembly comprising an A/D converter circuit, and a transducer array, the transducer assembly weighing less than one pound;
- a wire connecting said body and said transducer assembly, the wire having a path for feeding power from the power supply to the transducer assembly, and a signal path for transmitting digital signals between the system electronics and the transducer assembly; and
- a digital beam former.

15. The lightweight diagnostic ultrasound instrument as described in claim 14, wherein said controller comprises a D-controller.

16. The lightweight diagnostic ultrasound instrument of claim 14, further comprising a holster for retaining a transducer assembly.

17. The lightweight diagnostic ultrasound instrument as described in claim 14, wherein said body is a balance body.

18. The lightweight diagnostic ultrasound instrument as described in claim 14, wherein said body comprises an aperture and internal components arranged such that said body is balanced for comfortable holding in the user's hand.

19. The lightweight diagnostic ultrasound instrument as described in claim 14, wherein said body is configured so that the user's palm and fingers support the weight of said body by being essentially flat against a backside of said body.

20. The lightweight diagnostic ultrasound instrument as described in claim 14, wherein said system electronics package comprises said digital beam former.

21. The lightweight diagnostic ultrasound instrument as described in claim 14, wherein said transducer comprises said digital beam former.

22. The lightweight diagnostic ultrasound instrument as described in claim 14, wherein the display screen is a touch screen.

23. The lightweight diagnostic ultrasound instrument as described in claim 22, wherein the touch screen responds to a series of on screen commands and is reprogrammable for hot menus.

24. The lightweight diagnostic ultrasound instrument as described in claim 22, wherein the touch screen further comprises a QWERTY style keypad.

25. A medical ultrasound system comprising:
- a balance body, which has a center of gravity positioned close to a strength of a user's hand when the ultrasound instrument is held by the user, said balance body incorporating system electronics, a power supply and a user interface wherein said user interface comprises a controller and a touch screen; and
- a transducer assembly wirelessly connected to said balance body, wherein the system electronics comprises:
  - a digital beam former, an image processor, and a first digital signal processor capable of processing B mode, M mode and flow (2D Doppler) scans; and
  - a second digital signal processor comprising:
    - a digital Doppler QBP filter for filtering PW Doppler signals; and
    - a digital signal processor core for PW Doppler signal processing, wherein the first digital signal processor and the second digital signal processor are integrated into a single application specific integrated circuit (ASIC).

* * * * *